(12) United States Patent
Piñol Ribas et al.

(10) Patent No.: US 7,722,882 B2
(45) Date of Patent: May 25, 2010

(54) LIVE ATTENUATED VACCINE AGAINST PORCINE PLEUROPNEUMONIA

(75) Inventors: Jaume Piñol Ribas, Valldoreix (ES); Sergi Bru Virgili, Barcelona (ES); Enric Espuña Maso, Olot (ES); Enrique Querol Murillo, Barcelona (ES)

(73) Assignee: Laboratorios Hipra, S.A., Amer (ES)

( * ) Notice: Subject to any disclaimer, the term of this patent is extended or adjusted under 35 U.S.C. 154(b) by 625 days.

(21) Appl. No.: 10/535,416

(22) PCT Filed: Nov. 17, 2003

(86) PCT No.: PCT/EP03/12839

§ 371 (c)(1),
(2), (4) Date: May 19, 2005

(87) PCT Pub. No.: WO2004/045639

PCT Pub. Date: Jun. 3, 2004

(65) Prior Publication Data

US 2006/0051371 A1    Mar. 9, 2006

(30) Foreign Application Priority Data

Nov. 20, 2002    (ES) ................................ 200202663

(51) Int. Cl.
*A61K 39/02* (2006.01)
*C07H 21/02* (2006.01)
*C12N 1/12* (2006.01)

(52) U.S. Cl. ................. 424/200.1; 536/23.1; 435/252.1
(58) Field of Classification Search ............... 424/200.1
See application file for complete search history.

(56) References Cited

U.S. PATENT DOCUMENTS 6,019,984 A * 2/2000 MacInnes et al. ........ 424/255.1
6,472,183 B2 * 10/2002 Prideaux et al. ............ 435/71.1

OTHER PUBLICATIONS

Reimer et al. Microbial Pathogenesis vol. 18, pp. 197-209, 1995.*
Ellis, R.W. (Chapter 29 of "Vaccines" Plotkin, S.A. et al. (eds) published by W.B. Saunders company (Philadelphia) in 1988.*
Boslego et al., Chapter 17, 1991.*
Dorland's Medical Dictionary (29th Edition, 2000).*
Reimer et al, *Microbial Pathogenesis*, 18:197-209 (1995).
Frey et al, *Gene*, 142:97-102 (1994).
Jansen et al, *Infection and Immunity*, 62(10):4411-4418 (1994).
Tascon et al, *Molecular Microbiology*, 14(2):207-216 (1994).

* cited by examiner

*Primary Examiner*—Robert Mondesi
*Assistant Examiner*—Khatol Shahnan-Shah
(74) *Attorney, Agent, or Firm*—Sughrue Mion, PLLC

(57) ABSTRACT

The present invention provides a method for obtaining an immunogenic, non-haemolytic strain of *Actinobacillus pleuropneumoniae* which is modified, at least in a segment of the apxIA gene and optionally in a segment of the apxIIA gene that encodes a transmembrane domain of the Apx haemolytic and cytolytic exotoxins. It comprises also the strains, and the attenuated live vaccine porcine pleuorpneumonia obtained therewith.

17 Claims, 6 Drawing Sheets

Figure 2:
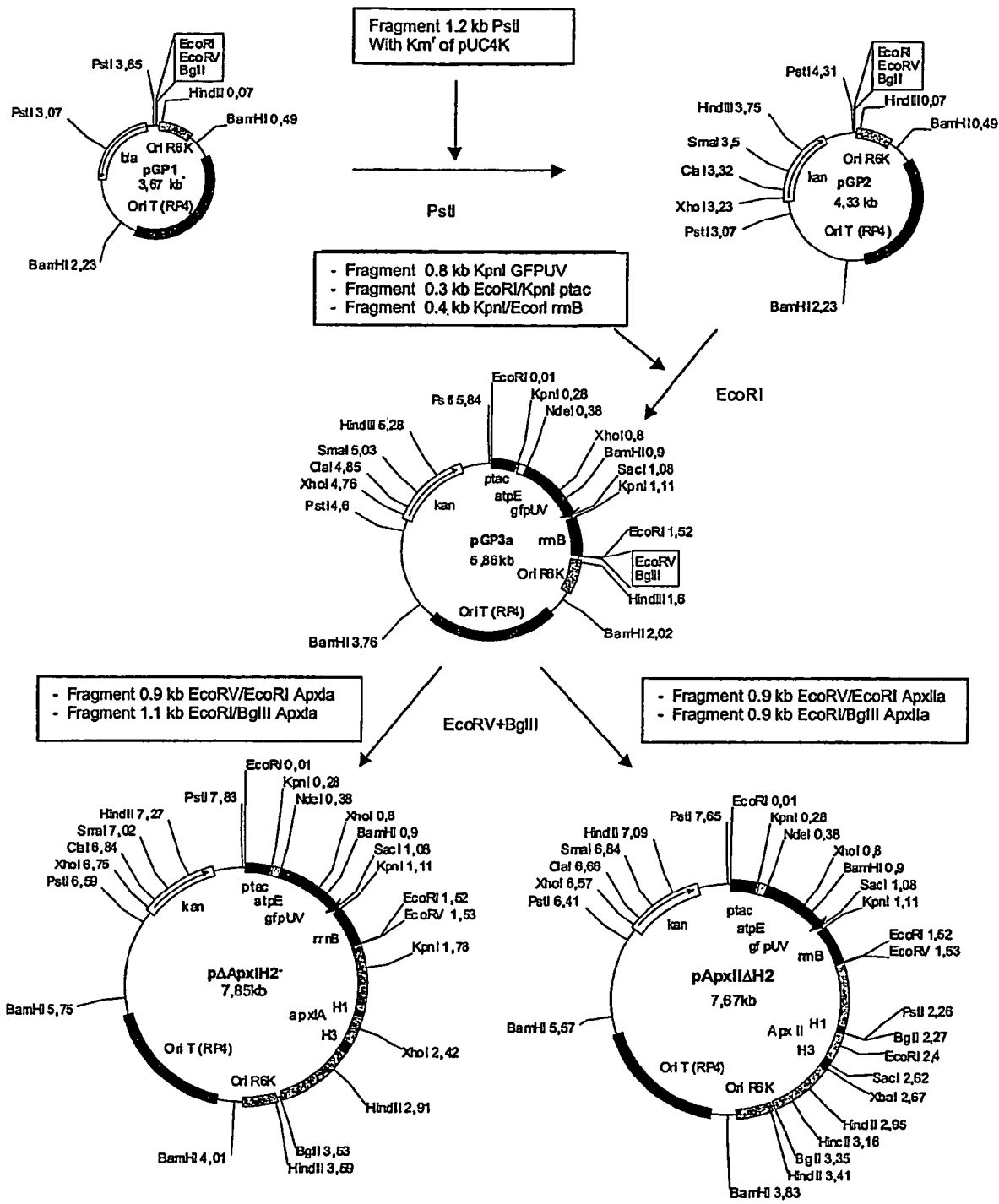

```
ApxIA    MANSQLDRVKGLIDSLNQHTKSAAKSGAGALKNGLGQV----KQAGQKLILYIPKDYQAS  56
ApxIIA   MSKITLSSLKSSLQQGLKNGKNKLNQAGTTLKNGLTQTGHSLQNGAKKLILYIPQGYDSG  60
         *::   *. :*. ::.   ::  *.  :...  :*****  *.    ::...:********:.*::.

ApxIA    TGSSLNDLVKAAEALGIEVHRSEKNGTALAKELFGTTEKLLGFSERGIALFAPQFDKLLN  116
ApxIIA   QGNGVQDLVKAANDLGIEVWREERSNLDIAKTSFDTTQKILGFTDRGIVLFAPQLDNLLK  120
         *..:;******;  *****  *.*;..    :**   *.**;*;***;;***.*****;*;**;

ApxIA    KNQKLSKSLGGSSEALGQRLNKTQTALSALQSPLGTAIAGMDLDSLLRRRRNGEDVSGSE  176
ApxIIA   KNPKIGNTLG-SASSISQNIGKANTVLGGIQSILGSVLSGVNLNELLQNK----DPNQLE  175
         ** *:.::** *:...:.*.::.*;:.*..:**:**:...:;**:;*;.**::.:  *.*

ApxIA    LAKAGVDLAAQLVDNIASATGTVDAFAEQLGKLAMPYLTLA-LSGLASKLNNLPDLSLAG  235
ApxIIA   LAKAGLELTNELVGNIASSVQTVDAFAEQISKLGSHLQNVKGLGGLSNKLQNLPDLQKAS  235
         *****:.*;  :**.****:.  ********;.**.     .:  *.**;.**:*****.*.
                    H1
ApxIA    PGFDAVSGILSVVSASFELSNKDADAGTKAAAGIEISTKILGNIGKAVSQYIIAQRVAAG  295
ApxIIA   LGLDIISGLLSGASAGLILADKEASTEKKAAAGVEFANQIIGNVTKAVSSYILAQRVASG  295
         *;* ;*;;** .**;**;;**;*.: .*****;*;;..;**:**; **** ** ***** :*
                           H2
ApxIA    LSTTAATGGLIGSVVALAISPLSFLNVADKFERAKQLEQYSERFKKFGYEGDSLLASFYR  355
ApxIIA   LSSTGPVAALIASTVALAVSPLSFLNVADKFKQADLIKSYSERFQKLGYDGDRLLADFHR  355
         **:*.....**.*.****:************::*. ::.****;*:**;** ***.*;*
                                H3
ApxIA    ETGAIEAALTTINSVLSARSAGVGAAATGSLVGAPVAALVSAITGIISGILDASKQAIFE  415
ApxIIA   ETGTIDASVTTINTALAAISGGVGAASAGSLVGAPVALLVAGVTGLITTILEYSKQAMFE  415
         ***.*:*.*: :****;.*:* *.*****;:********  **:;.**:*:  ****.**

ApxIA    RVATKLANKIDEWEKKHGKNYFENGYDARHSAFLEDTFELLSQYNKEYSVERVVAITQQR  475
ApxIIA   HVANKVHDRIVEWEKKHNKNYFEQGYDSRHLADLQDNMKFLINLNKELQAERVVAITQQR  475
         :**.*: ::* *******.*****.*****;***;**  *  *:*.;:;* :  ***  ..**********

ApxIA    WDVNIGELAGITRKGSDTKSGKAYVDFFEEGKLLEKEPDRFDKKVFDPLEGKIDLSSIN-  534
ApxIIA   WDNQIGDLAAISRRTDKISSGKAYVDAFEEGQHQSYDSS----VQLDNKNGIINISNTNR  531
         ** ;**;**.*;*;*  ..  ****** ****:   .  :..     :*  :*  *;:*.  *

ApxIA    KTTLLKFVTPVFTAGEEIRERKQTGKYQYMTELFVKGKEKWVVTGVQSHNAIYDYTNLIQ  594
ApxIIA   KTQSVLFRTPLLTPGEENRERIQEGKNSYITKLHIQRVDSWTVTDGDAS-SSVDFTNVVQ  590
         **  : * **::*.*** *** * *  ** .*:*:*.::  :.*.**. ::   *:**;:*
```

Fig. 1

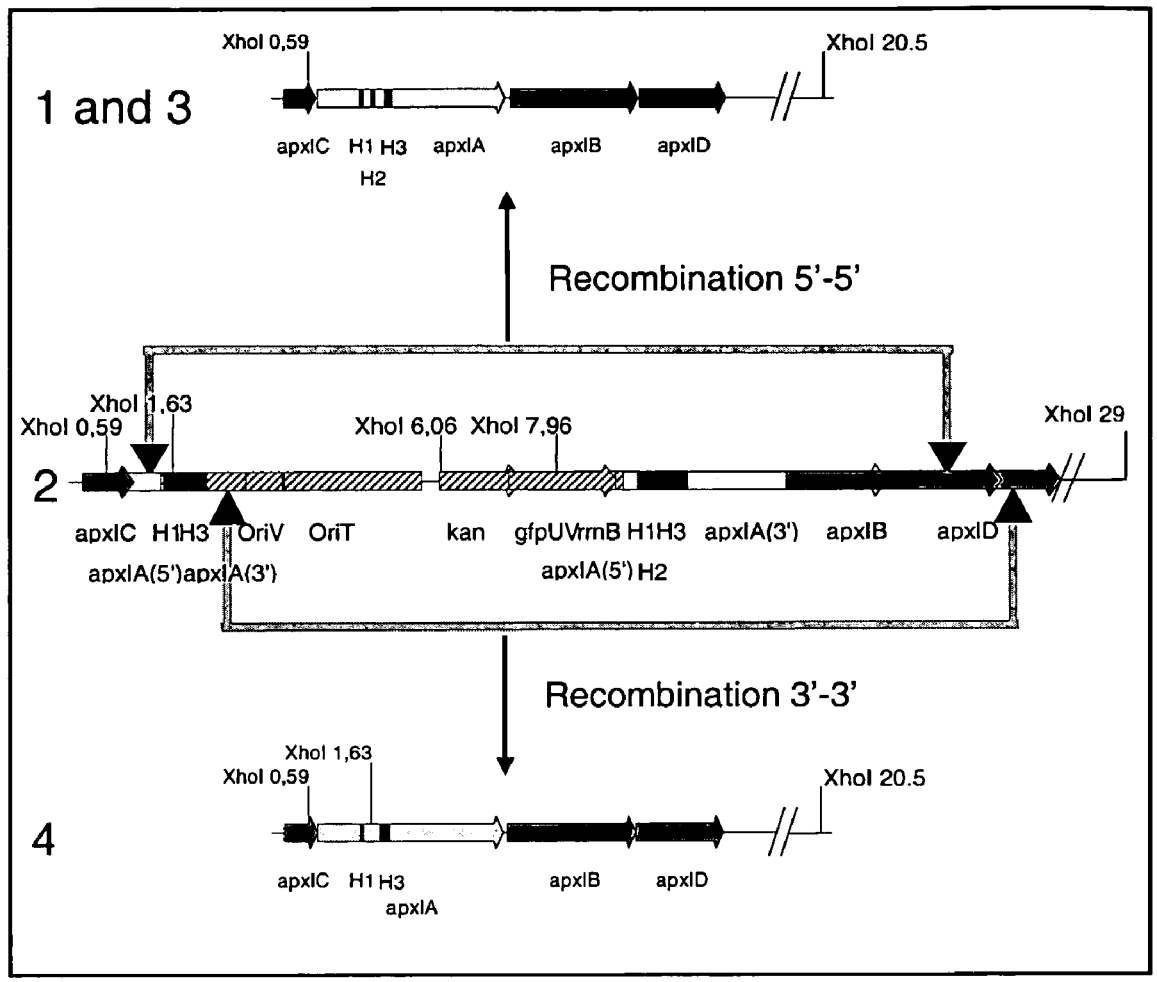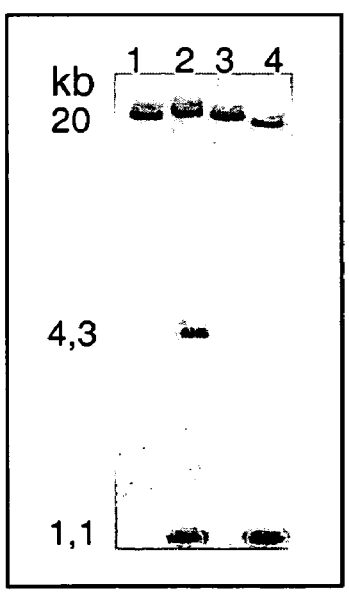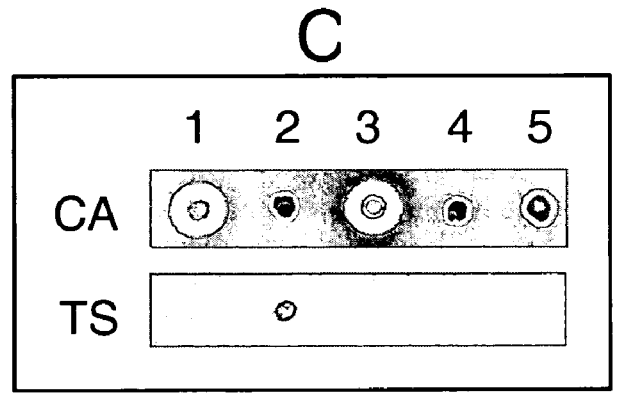
Fig. 3

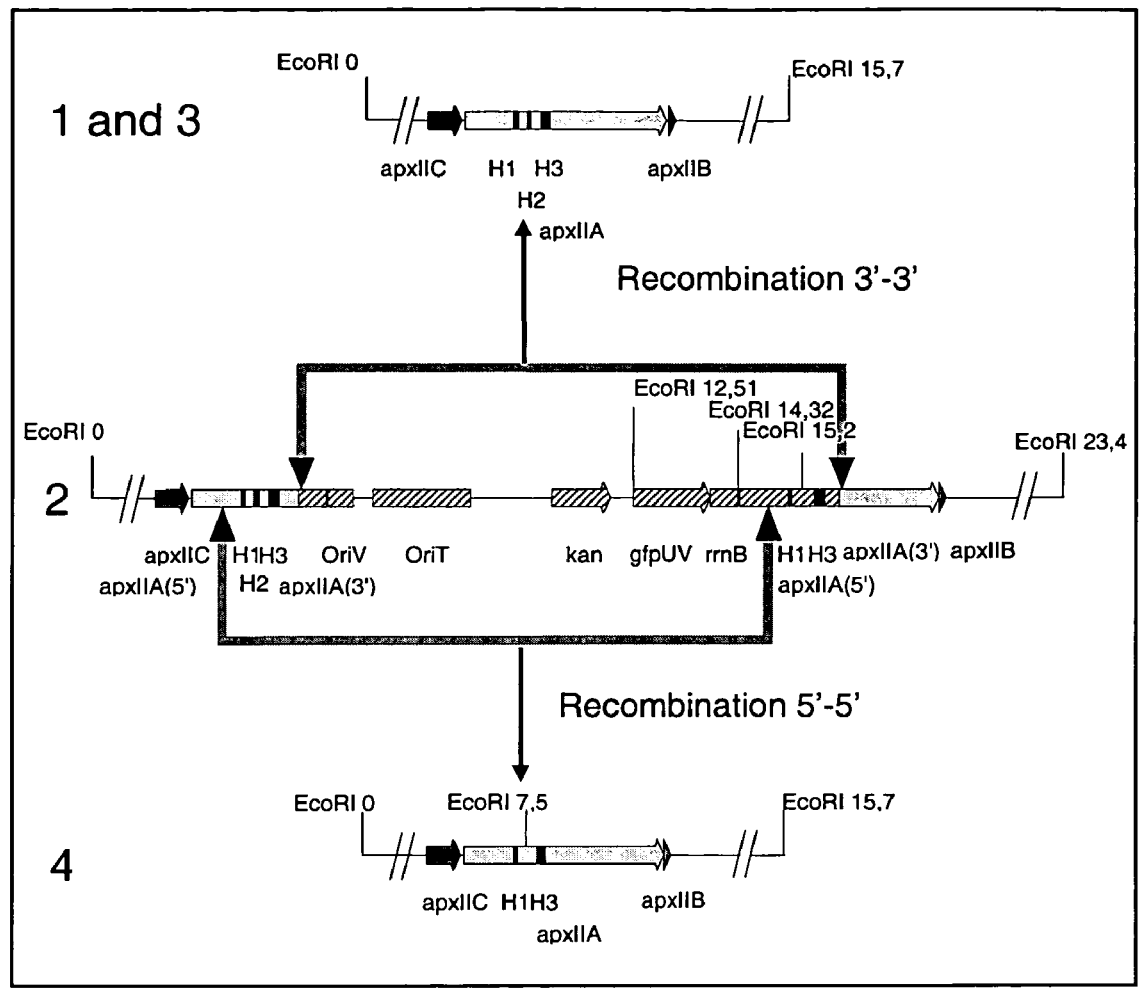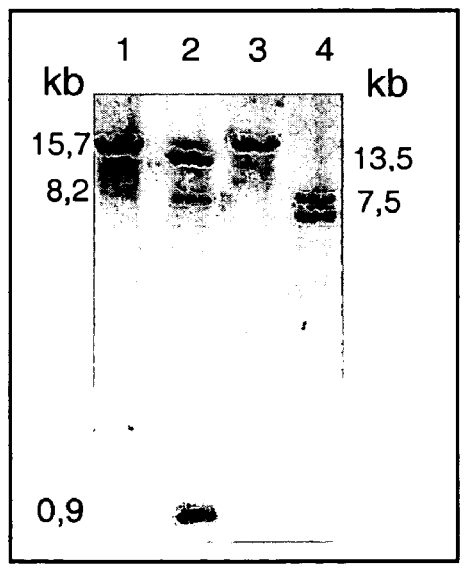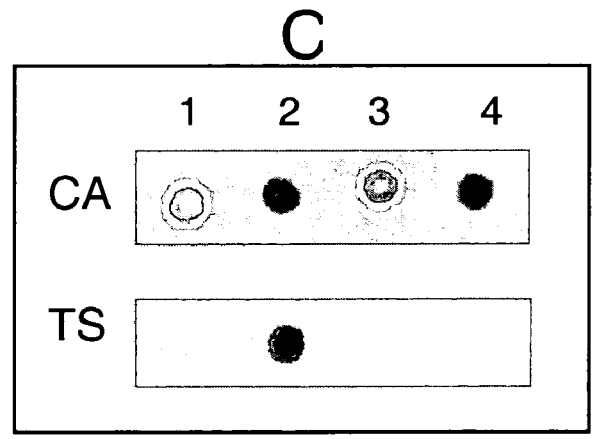
Fig. 4

LIVE ATTENUATED VACCINE AGAINST PORCINE PLEUROPNEUMONIA

This Application is a 371 of PCT/EP2003/012839, filed Nov. 17, 2003; the disclosure of which is incorporated Herein by reference.

FIELD OF THE INVENTION

The present invention relates to a method for obtaining an immunogenic, non haemolytic strain of *Actinobacillus pleuropneumoniae*, suitable to prepare a live attenuated vaccine against porcine pleuropneumonia.

BACKGROUND OF THE INVENTION

*Actinobacillus pleuropneumonia* (thereafter "App") is a Gram-negative bacteria which causes porcine pleuropneumonia, a worldwide distributed infectious disease responsible of important Economic losses in the swine industry.

The App most important virulence factors are extracellular proteins namely: Apx exotoxins. These exotoxins belong to the pore-forming RTX toxins family, widely spread among pathogenic gram-negative bacteria The main exotoxins in App are: ApxI, ApxII, ApxIII and ApxIV.

Exotoxins ApxI and ApxII are haemolytic and cytolytic. ApxI shows a strong haemolytic and cytolytic activity and ApxII shows a weak haemolytic and a moderate cytolytic activity.

Although all, so far screened, serotypes are able to produce ApxIV, there is a characteristic serotype distribution for the expression of the rest of the Apx exotoxins. Serotypes 1, 5, 9 and 11 produce exotoxins ApxI and ApxII; Serotype 10 only produces ApxI; Serotypes 7 and 12 produce only ApxII and serotypes 2, 3, 4, 6, and 8 produce ApxII and ApxIII.

The genes corresponding to exotoxins ApxI and ApxII are organized as operons. The operon of of the ApxI exotoxin contains 4 genes: apxIC, apxIA, apxIB and apxID. The gene of apxIA codes for the ApxI exotoxin itself The gene apxIC codes for an activator protein (acylase) which introduces a post-translational modification (acylation) in the Apx, which allows the ApxI to acquire an active conformation, making it able for the interaction with the host specific cell receptors. The apxIB and apxID genes code two membrane proteins which secrete the mature ApxI exotoxin to the external medium.

The ApxII operon contains only the gene A (apxIIA) and gene C (apxIIC) which code, respectively, for ApxII and for the acylase responsible for the ApxII to acquire an active conformation. There exists also a small fragment which shows a certain similarity with the apxIB gene but it does not originate a functional protein. The export of the mature ApxII to the external medium is due to the action of the proteins encoded by the apxIB and apxID genes.

The present vaccination methods do not provide a complete protection against all App serotypes.

Patent WO97/16532A1 describes the construction of a vaccine strain able to induce an immunological response in an animal. This comprises a modified microorganism which produces a partially or totally inactivated Apx toxin, due to a partial deletion. This deletion, done by induced mutagenesis of the structural gene apxIA and/or to the partial deletion of an apxIIC activator gene. It does not modify the transmembrane zone.

Patent EP810283A2 describes the construction of an App vaccine strain by modifying the ApxIC gene in such a way that this does not produce the activator protein in a functional form and this can not activate the toxin by acylation. It neither modifies the transmembrane zone.

Jansen et al. (Infection and Immunity 63: 7-37 (1995)) described the production of App homologous recombinants by site directed mutagenesis.

These mutants present the apxIA gene which is inactivated by insertion of the CMr gene and/or the apxIIA gene inactivated by insertion of the TETr gene.

Tascón et al. (Molecular Microbiology 14: 207-216 (1994)) describes two App mutants. One of them has a disruption in the gene apxIBD and the other a disruption in the structural gene apxIA.

Reimer et al; (Microbial Pathogenesis 18: 197-209 (1995)) describes an App. a virulent mutant which, by chemical mutagenesis, has deletions that affect important parts of the operon apxIABCD. This mutant does not synthesize the ApxI toxin, but is able to synthesize the ApxII, although this is not secreted from the cell.

Strains that do not express ApxI and ApxII exotoxins can not be used as attenuated vaccines because they do not induce protective immune responses since the ApxI and ApxII exotoxins are one of the most important virulence determinants of App.

Prideaux (The 16th International Pig Veterinary Society Congress, Melbourne (Australia) 17-20th September 2000, pag. 439-442)) describes a vaccine prepared from a strain with an inactivated apxIIC gene that secretes and express a non-activated ApxII toxin unable therefore to attach to the target cells.

So, the live attenuated vaccines described in the previous background of the invention, based on App strains without haemolytic capability, are less immunoprotective because they have suffered modifications in their structure that do not allow them to attach to the membrane receptor of the target cells. Furthermore these can not generate antibodies against ApxI and/or ApxII toxins, since these are not secreted by the cell. Frey et al. (Gene 142: 97-102 (1994)) describe the amino-acid sequence of the ApxI exotoxine from a serotype I strain and Smiths et al.; (Infection and Immunity 59: 4497-4504 (1991)) describe the amino-acid sequence of the ApxII exotoxin of a serotype 9 strain.

SUMMARY OF THE INVENTION

The authors of the present invention have discovered a method to obtain an immunogenic and non-haemolytic App strain from an App virulent strain which has been modified in at least one segment of apxIA gene (SEQ ID NO 1) and optionally in a segment of the apxIIA gene (SEQ ID NO 2) which code a transmembrane domain of the Apx cytolytic and haemolytic exotoxins.

This strain has no haemolytic activity, but maintains unaltered its immunoprotective ability and is suitable to prepare a live attenuated vaccine against porcine pleuropneumonia.

The transmembrane domains of ApxI and ApxII exotoxins play an important role in the formation of the pore in the membrane of the target cell. Once this pore has been formed, osmotic imbalances develop which eventually cause the lysis of the target cell.

Surprisingly it has been found, that the live attenuated vaccine prepared with these App modified strain may be administered at low dosage, that contains ApxI and ApxII toxins without haemolytic activity and that contains all the antigenes immunologically necessary to obtain a strong immunogenic response.

The object of the present invention is to develop a method to obtain an immunogenic and non-haemolytic App strain from a virulent App. strain modified in at least one segment of apxIA gene and optionally in a segment of apxIIA gene which codes a transmembrane domain of the haemolytic and cytolytic Apx exotoxins.

Furthermore, another aspect of the present invention are the strains to be obtained using the methods object of the present invention and the vaccines prepared therefrom.

In a third aspect the invention aims at the App strains deposited in the Colección Española de Cultivos Tipo with the registration numbers: CECT 5985 and CECT 5994.

DESCRIPTION OF THE FIGURES

FIG. 1.

FIG. 1 shows an alignment performed with the ClustalX program (Thompson et al; Nucleic acid Research 24:4876-4882 (1997)) between the amino-acid sequences of ApxI coming from a serotype 1 strain (Frey et al; Gene 142: 97-102 (1994))and ApxII from serotype 9 (Smits et al.; Infection & Immun. 59:4497-4504 (1991)). In this figure only the sequence contained between amino-acids 1 to 594 of ApxI and 1 to 590 of ApxII have been enclosed. On the alignment the following regions are framed: H1 (amino-acids 233 to 253), H2 (amino-acids 296 to 315) and H3 (amino-acids 369 to 405). These regions correspond respectively to the three transmembrane domains present in both Apx.

FIG. 2.

FIG. 2 shows a scheme with the steps followed to obtain the hybrid plasmids pApxIΔH2 and pApxIIΔH2. Firstly, the pGP1 plasmid was obtained by digestion of plasmid pGP704 ((Miller and Mekalanos; J. Bacteriol. 170: 2575-2583 (1988)) with restriction enzymes EcoRI and BglII and subsequent ligation of the oligonucleotides pGP5' and pGP3'. This plasmid contains the vegetative origin of replication of plasmid R6K (OriR6K) and the origin of transference by conjugation of plasmid RP4 (OriTP4) and of the gene of resistance to ampicilin (Bla). Plasmid pGP1 was digested with the restriction enzyme PstI and ligated with a fragment PstI carrier of a gene of resistance to Kanamicin ($Km^r$ or Kan) which comes from plasmid pUC4K to originate plasmid pGP2. To this plasmid, previously dephosphorylated and digested with restriction enzyme EcoRI, three DNA fragments amplified by PCR were inserted namely: the promoter ptac, the coding region of the fusion at atpE/GFPUV (ribosome binding region where the *E. coli* atpE with the U.V. variant of the green fluorescence protein) and the transcription rrnB terminator.

The resulting plasmid was named pGP3. In the plasmid, the flanking regions 5' and 3' (amplified by PCR) that code for the second transmembrane helix of genes apxI and apxII were inserted to form plasmids pApxIΔH2 and pApxII ΔH2 respectively.

FIG. 3.

FIG. 3 is divided in three panels: Panel A shows the restriction maps in kilobases ( kb) and the distribution of the genes in the operon apxI from the genome of App. In light gray, the apxIA gene is depicted, being the target of the different recombination events, and in dark gray the adjacent genes apxIC, apxIB and apxID. The different genes or regions of plasmid pApxIΔH2 are drawn using skewed bars. The coding fragments of the transmembrane helices (H1, H2 and H3) of apxIA are highlighted in Black. The names and some detailed structures in FIG. 2 plasmids have been simplified. Thus gfpUV comprises the ptac promoter and the atpE/GFPUV fusion; OriV indicates the vegetative origin of replication of R6K and OriT the origin of transference by conjugation of RP4. In (1) and (3) both are shown the restriction map obtained with enzyme XhoI and the distribution of the genes of operon ApxI of the App genome are shown. In (2) the restriction map of the same operon after the insertion of plasmid pApxIΔH2 in the App genome is shown. This insertion occurs by a unique homologous recombination event between flanking regions 5' of H2 placed in plasmid pApxIΔH2 and the App genome respectively.

Panel B of FIG. 3 shows the results of the hybridisation of an Apx1 gene probe with a southern transference of the digested genomic DNA digested with XhoI and obtained from the harvests of: 1) HP816 $N1^r$; 2) recombinant obtained by insertion of plasmid pApxIΔH2 in the App genome through a unique homologous recombination event between the flanking regions 5' of H2 (HP816R1); 3) recombinant obtained from HP816R1 which recovers the same phenotype of the parent strain HP816 $N1^r$ and 4) recombinant obtained from HP816R1 which recovers the same phenotype of the parent strain HP816 $N1^r$ with the exception that it shows the same haemolytic activity than the HP816R1 ($AppApxIH2^-$).

Panel C shows the aspect of the colonies seeded from the same cultures described in panel B (1, 2, 3 and 4) together with another colony coming from a serotype 7 App culture (5). The colonies were seeded on Columbia blood agar plates supplemented with 0.004% NAD (CA)or in TSYN plates supplemented with 25 μg/mL kanamicin (TS). The presence of large haemolytic halos surrounding the colonies of cultures 1 and 3 and of small haemolytic halos surrounding the colonies in cultures 2, 4 and 5 can be seen in CA. Also the absence of growth in TS of cultures 1, 3, 4 and 5.

FIG. 4

FIG. 4 is divided in 3 panels: Panel A shows the restriction maps (in kb) and the distribution of the genes in operon apxII located in the App genome. In light grey the apxIIA gene is depicted. This is the target of the different recombination events. The adjacent genes apxIIC, apxIIB are depicted in dark grey; The different genes or regions of plasmid pApxIIΔH2 are drawn using skewed bars. The coding fragments of the transmembrane helices (H1, H2 and H3) of apxIIA are highlighted in black. The restriction map obtained with the enzyme EcoRI and the distribution of the ApxII operon genes of the App genome are shown in (1) and (3). The restriction map of the same operon after the insertion of pApxIIΔH2 plasmid in (2) is depicted. This insertion is done through a unique homologous recombination event between the 3' flanking regions of H2 located in plasmid pApxIIΔH2 and the App genome. In (4) the restriction map of the operon is depicted after the resolution of the plasmid inserted in (2) after a second recombination through the 5' flanking regions of H2 located in the App genome.

Panel B shows the hybridisation results of a probe of gene apxIIA on a Southern transfer of the genomic DNAs digested with EcoRI and obtained from the following cultures of: 1) HP8816 $N1^r$ 2) Recombinant obtained by insertion of plasmid pApxIIΔH2 in the genome of App through a unique homologous recombination event between the 5' flanking regions of H2 (HP816R2); 3)recombinant obtained from HP816R2 which recovers the same phenotype of the parent strain HP816 $N1^r$; 4) recombinant obtained from HP816R2 which recovers the same phenotype of the parent strain HP816 $N1^r$ with the exception that it shows the same haemolytic activity than HP816R2 ($AppApxI/IIH2^-$).

Panel C shows the aspect of the colonies seeded from the same cultures described in panel B (1, 2, 3 and 4). The colonies were seeded in Columbia blood agar plates supplemented with NAD (CA), or in TSYN plates supplemented with 25 μ/mL of kanamycin (TS). The presence of small haemolytic halos surrounding he colonies of cultures 1 and 3 and the absence of haemolytic halos surrounding the colonies of cultures 2 and 4 can be seen. See also, in TS, the absence of growth of cultures 1, 3 and 4.

FIG. 5

Figure 5:
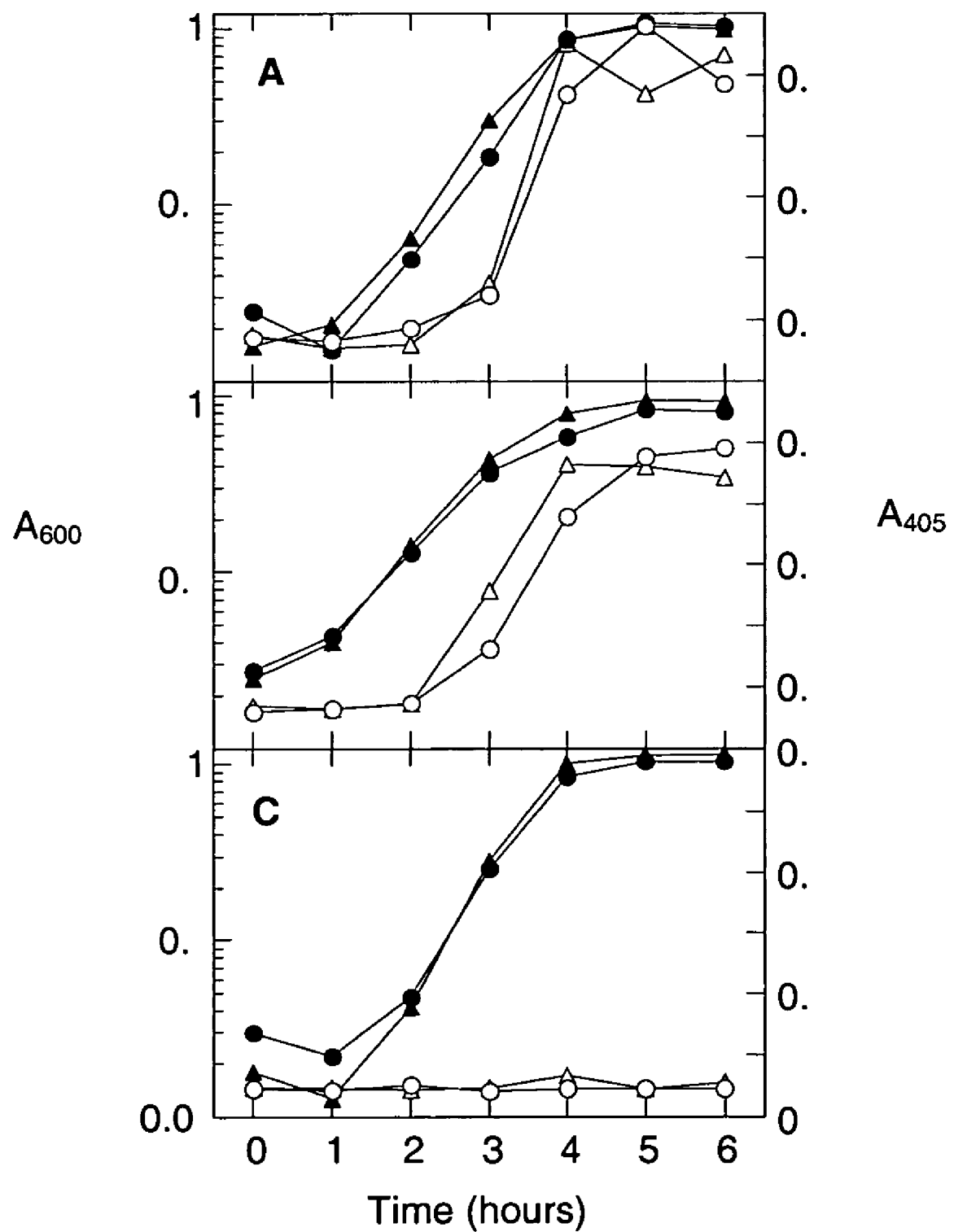

FIG. 5 shows three graphs with the growth curves, represented (dark symbols) from the absorbance values, at 600 nm, of the different cultures, at a one hour intervals (left y-axe). Simultaneously, several samples were taken from the supernatants of the cultures in the same time intervals. These samples were kept at 0 C. until these were diluted 1/50 in carbonate buffer (pH 9.6). These were then placed in microwells to quantify the presence of ApxI and ApxII by ELISA using a monoclonal antibody specific for each Apx. From the absorbance values, at 405 nm, of each tested sample (right y-axis), the curves were drawn representing the accumulation of each one of the Apxs along the time (light symbols). In (A) a HP816 N1′ culture-triangles- and an AppApxIH2⁻ culture-circles-; the light symbols show the ApxI accumulation. In (B) a culture of HP816 N1′-triangles- and an AppApxI/IH2⁻ culture-circles- the light symbols show the accumulation of ApxII. In (C), a culture of HP816RI-triangles- and, a culture of HP816R2 culture-circles- show the accumulation of ApxI and the light circles show the accumulation of ApxII.

FIG. 6

Panel (A) shows a Coomassie blue staining of a denaturing electrophoresis in polyacrilamide gel with samples of the supernatants of cultures taken at 5 hours from 1) HP816 N1′; 2) AppApxIH2⁻; 3) a control obtained from an App serotype 4 (the App serotype 4 produces and secretes the ApxII of 105 kD and ApxIII of 115 kD but not the ApxI); and M) marker of a molecular mass (the relevant bands of 110 and 120 kD are indicated). In (B) we can observe a Western-blot of a gel with identical samples to those analysed in gel (A) detected by means of a monoclonal antibody specific for the ApxI. In (C) we can observe a Western-blot of a gel with identical samples to those of gel (A) with the exception of track 2, which contains a sample of the supernatant of AppApxI/IH2⁻ culture. No picture of the gel is enclosed since the band distribution is identical to that which appears in gel (A). This transfer was revealed using a specific monoclonal antibody for ApxII. Observe that the band of 105 kD of track 3 appears detected only in (C).

DETAILED DESCRIPTION OF THE INVENTION

The invention refers to a method to obtain an immunogenic and non-haemolytic strain of *Actinobacillus pleuropneumoniae* from a virulent App, characterized by the following stages:

The transmembrane domains of the Apx haemolytic and cytolytic exotoxins are determined.

At least one fragment of gene apxIA is modified and optionally a segment of the apxIIA gene which codes a transmembrane domain of the Apx haemolytic and cytolytic Apx exotoxins.

The term immunogenic means that the App strain obtained with the method of the present invention maintains unaltered its immunoprotective ability, this means that it contains all antigens immunologically necessary to obtain a high immunogenic response in the host.

The term non-haemolytic means that the App strain, obtained with the method of the present invention, has no haemolytic activity, being an a virulent strain.

The choice of an App virulent strain, obtained from infected animals which suffer the disease, is done according to the usual methods known by those skilled in the art know.

The first step consists in the identification of the transmembrane domains of the App haemolytic and cytolytic Apx exotoxins using the TransMem programs (Aloy et al; Comp. Appl. Biosc. 13: 213-234 (1997)) or Helixmem (Eisenbeg et al.; J. Mol. Biol. 179: 125-142 (1984)) which analyses the amino-acid sequences of the haemolytic and cytolytic Apx exotoxins, as described for *E. coli* in Ludwig et al.; Mol. Gene. Genet. 226: 198-208 (1991).

The second stage consists in modifying at least one segment of the apxIA gene and optionally a segment of apxIIA gene which code a transmembrane domain of the Apx haemolytic and cytolytic exotoxins.

The term "modify" refers to the modification of a gene either by using DNA recombinant conventional techniques which include: the substitution of one or several nucleotides, the insertion of one or several nucleotides, the partial or total deletion of a gene, or through the disruption by chemically or radiation induced mutagenesis.

In a preferred realization, the modification is performed by deletion in, at least, one segment of apxIA gene and optionally in a segment of apxIIA gene, which code a transmembrane domain of the haemolytic and cytolytic Apx exotoxins.

The transmembrane domains, present in the apxIA and in apxIIA genes of the haemolytic and cytolytic exotoxins, were detected using the Transmem and Helixmem programmes above mentioned. The prediction performed on the amino-acid sequences of the haemolytic and cytolytic exotoxins ApxI and ApxII indicate that the transmembrane domains, also named transmembranes, are found located in the following zones of the sequence of the exotoxins:

First transmembrane domain H1: between amino-acids 233 and 253 corresponding to the nucleotides 697 to 759 from apxI.

Second transmembrane domain H2: between amino-acids 296 and 315, corresponding to nucleotides 886 to 945 from apxI Third transmembrane domain H3: between amino-acids 369 to 405, corresponding to nucleotides 1105 to 1215 from apxI In a preferred realization, the modification is carried out by means of a deletion in the segment of gene apxIA which codes the second transmembrane domain of the exotoxin ApxI of App.

The modification is carried out, preferably, by deletion of the nucleotides 886 to 945 of the apxIA gene which code the second transmembrane domain of the App ApxI exotoxin.

Another preferred realization, of the method object of the present invention, furthermore introduces an additional deletion in the segment of apxIIA gene which codes the second transmembrane domain of the ApxII exotoxin of App. Preferably a deletion of nucleotides 886 to 945 of gene apxIIA, which code the second transmembrane domain of the App ApxII exotoxin.

In the preferred realization form of the present invention, which will be described in detail in the section "examples", the achievement of an immunogenic non-haemolytic App strain has been performed using a process comprising the following steps:

A—Selection of an App virulent strain.

B—Prediction of the alfa helices of the transmembrane domain of the ApxI and ApxII proteins in order to design a nucleotide construction which allows the deletion in the second transmembrane domain of both proteins without affecting the folding process and the capacity of the resulting haemolysins to interact with the membrane specific receptors.

C—Construction of a cloning vector able of integrating in the App genome and which contains marker genes which allow the monitoring, in an efficient manner, the integration of such a vector.

C1—Construction of the hybrid plasmid pGP3 which has an origin of replication RK6, the RP4 origin of transfer and a gene of resistance to kanamycin. Furthermore, the gene of the fluorescent protein GPVUV (thereafter GFP) was enclosed, under the control of promoter ptac and terminator rrnB. The multiple cloning site was also modified to ease the later insertion of the DNA sequences.

C2. Construction of a hybrid cloning vector which contains the 5' and 3' flanking sequences of the second transmembrane helix, specified by the apxIA gene. Therefore, the hybrid plasmid pApxIΔH2 was constructed in order to select and clone such fragments adjacent to the 5' and 3' ends of the segment that codes the second transmembrane helix in the apxIA gene. This plasmid was used as the final vector for the transformation of App.

C.3. Construction of a hybrid donation vector which contains the 5' and 3' flanking sequences of the second transmembrane helix specified by the apxIIA gene. Therefore the hybrid plasmid pApxIIΔH2 was constructed in order to choose and clone such fragments adjacent to the 5' and 3' ends of the segment that codes the second transmembrane helix in the apxIIA gene. This plasmid was used as a final vector for the transformation of App.

D. Construction of the recombinant bacteria which have resolved the hybrid plasmid inserted in the genome.

D.1. Construction of the App recombinant strain named HP816R1, which incorporates the hybrid plasmid pApxIΔH2 in the App genome as a result of a unique homologous recombination event between such plasmid and the genome of App HP816 N1$^r$ which is a strain resistant to nalidixic acid obtained from a spontaneous mutant of the App BP816 strain.

D.2 Construction of the strain AppApxIH2$^-$ using a procedure that allows, once the recombinant bacteria obtained in step 1 have been identified, to resolve the recombinant vector integrated in the genome through a second homologous recombination event, as well as to detect and isolate the bacteria that, due to this second recombination, have achieved the partial deletion in the apxIA gene.

D.3 Construction of the App HP816R2 recombinant strain, which incorporates the hybrid plasmid pApxIIΔH2 in the genome of AppApxIH2$^-$ as a result of a unique homologous recombination event between such plasmid and the genome of AppApxIH2$^-$.

D.4 Construction of the AppApxI/IIH2$^-$ strain using a procedure that allows, once the identified recombinant bacteria have been obtained in step D.3, to resolve the recombinant vector integrated in the genome by means of a second homologous recombination event, as well as to detect and isolate the bacteria that, due to the second recombination, have acquired the partial deletion in apxIIA gene.

In the present invention the obtained mutant AppApxIH2$^-$ is identical to the original wild type App strain, except for the deletion of nucleotides 886 to 945 (both inclusive) of the coding sequence of gene apxIA which corresponds with that absence of the amino-acids 296 to 315 (both inclusive) in the produced ApxI.

In the present invention the obtained mutant AppApxI/IIH2$^-$ is identical to strain AppApxIH2$^-$ except by the deletion of nucleotides 886 to 945 (both inclusive) of the coding sequence of gene apxIIA which corresponds with the absence of amino-acids 296 to 315 (both inclusive) in the ApxII produced.

In the preferred realization of the present invention the only modifications which are produced in the App genome are the deletion of 60 base pairs within the coding sequences of genes apxIA and apxIIA and the substitution of the same by restriction targets, in this case the corresponding to the enzymes XhoII and EcoRI respectively. No additional insertions of sequences coming from plasmidic DNA are produced (as for instance the gene of resistance to the kanamicin) in the App genome. This allows the obtained strain to be modified in the same gene o in another target gene following exactly the same strategy which was used to carry out the first modification. On the other hand, it avoids that the resulting strain be resistant to multiple antibiotics, which is a desirable characteristic in a strain to be used as live vaccine.

The restriction target used in the present invention is not critical. Although a construction could be used that introduced no restriction target, its use is preferable in order to have an additional mechanism to detect the desired recombinant clones and to be able to perform a follow up of the stability of the strain, or strains obtained. Therefore any target can be used proving that it does not introduce a stop codon of the protein synthesis and that gives rise to restriction fragments analysable by electrophoresis (i.e. more than 100 base pairs) with flanking restriction fragments which might exist previously in the App genome.

The invention refers also to an App strain obtained according to the above described method.

Another object of the invention is an App strain characterized because it has a deletion in nucleotides 886 to 945 of the apxIA gene, that code the second transmembrane of the ApxI exotoxin, deposited in the Colección Española de Cultivos Tipo (Spanish Collection of Type Cultures), Universidad de Valencia Edificio de Investigación Campus de Burjasot 46100 Burjast (Valencia) Spain, with the registration number CECT 5985 deposited on Jan. 10, 2002, according to the Treaty of Budapest of 28$^{th}$ Apr. 1977, or a mutant thereof.

Another object of the invention is an App strain characterized by having a deletion of nucleotides 886 to 945 of the apxIA gene that code the second transmembrane of the ApxI exotoxin and besides a deletion of nucleotides 885 to 944 of apxIIA gene that code the second transmembrane of the ApxII exotoxin deposited in the Colección Española de Cultivos Tipo (Spanish Collection of Type Cultures), Universidad de Valencia Edificio de Investigación Campus de Burjasot 46100 Burjasot (Valencia) Spain, with the registration number CECT 5994depsoited on Jun. 11, 2002, according to the Budapest Treaty, or a mutant thereof.

The invention also refers to the vaccines for the protection of the animals against porcine pleuropneumoniae. These vaccines may be prepared according to the usual methods known by those skilled in the art.

These vaccines comprise an immunologically effective amount of bacteria of a live App attenuated strain, obtained according to the method described in the present invention. Immunologically effective means that the amount of bacteria administered for the vaccination is sufficient to induce in the host an effective immunological response against an infection caused by virulent forms of App.

The dosage to be used will depend on the age and weight of the animal to be vaccinated and the administration form.

The vaccine may contain whichever bacterial dose sufficient to induce an immune response. The suitable dosage is comprised in the range $10^3$ and $10^{10}$.

The vaccine may contain furthermore a pharmaceutically acceptable excipient. This excipient may be as simple as water, but it may also comprise the culture fluid in which the bacteria are grown or a solution with a physiological concentration of salt.

Another example of pharmaceutically acceptable excipients, useful in the present invention enclose stabilizers, carbohydrates (i.e.: glucose, sacharose, manitol, sorbitol) and buffers (i.e.: phosphate buffers).

Optionally other adjuvant components may be added to the vaccine. These adjuvants are non-specific stimulants of the immune system which augment the immune response of the host against the pathogenic invader. Examples of adjuvants are: Vitamin E and vegetal oil.

The vaccine may be administered, to animals, by intranasal, intradermal, subcutaneous, spray or intramuscular routes.

The industrial application of the invention is easily deduced from the description. It is worth mentioning that porcine pleuropneumonia is a worldwide infectious respiratory disease responsible of severe economic losses to the porcine industry and that the method of the present invention to obtain immunogenic, non-haemolytic App strains allows the preparation of efficacious vaccines to fight porcine pleuropneumonia.

The examples that follow are described in order to provide, to the skilled in the art, a sufficiently comprehensive and complete explanation of the present invention, but these must not be considered as limitation to the essential aspects of the same as described in the previous section of this description.

EXAMPLE

The techniques and DNA recombinant methods applied as follows, are described in detail in Sambrook and Russell ((In Molecular cloning 3$^{rd}$ Ed. Cold Spring Harbor Laboratory Press, Cold spring Harbor N.Y. (2001) and Ausubel et al; *Current Protocols in Molecular Biology*, John Wiley and Sons, Inc. (1998)). All PCR products were previously cloned in a pBE plasmid before being digested with restriction enzymes. This plasmid is a derivative of pBluescript SK2 (STRATAGENE™) vector and presents the multiple cloning site substituted by a small nucleotidic sequence which specifies only the target of the restriction enzyme EcoRV.

The *E. coli* XL1-blue strain (STRATAGENE™) has been used as a host for hybrid vectors based on plasmids pUC118 or pBluescript SK. The *E. coli* S17-1 λ pir strain (Simon et al; Biotechnology 1:784-791 (1983)) has been used as a host of the hybrid vectors based in plasmid pGP704.

All the oligonucleotide sequences described hereunder are written in the sense 5' to 3' unless it is explicitly otherwise indicated. In all PCR reactions, the Deep Vent thermopolymerase (New England Biolabs), which has test correcting activity, was used.

A. Selection of a Virulent App Strain.

The HP816 strain, which corresponds to a natural type 1 serotype of App. belonging to Laboratorios Hipra S.A. (Amer-Girona-Spain), was chosen as a wild type App strain.

Strain HP816N1$^r$ is a strain resistant to nalidixic acid obtained from a spontaneous mutant of the wild type HP816.

B. Identification of the Transmembrane Domain of Exotoxins ApxI and ApxII.

The three transmembrane domain which adopt an α-helix structure, were determined by means of the use of programmes TransMem (Aloy et al; Comp. Appl. Biosc. 13:213-234 (1997)) and Helixmem (Eisenbeg et al; J. Mol. Biol. 179: 125-142 (1984)) as described for *E. coli* (Ludwig et al; Mol. Gene. Genet. 226:198-208 (1991)) applied to the amino-acid sequence of the ApxI coming from a serotype 1 strain (Frey et al; Gene 142: 97-102 (1994)) and the ApxII of a type 9 serotype (Smits et al; Infection and Immunity 59:4497-4504 (1991)). These programmes detected three regions which could act as transmembrane helices in both proteins (FIG. 1): the first transmembrane is located between amino-acids 233 and 253 (H1); The second transmembrane is located between amino-acids 296 and 315 H2) and the third transmembrane between amino-acids 369 and 405 (H3) all of them from ApxI.

C. Construction of Hybrid Cloning Vectors which are Able to Integrate in the App Genome.

In FIG. 2 we can see an outline with the maps of the plasmids which are described in this section.

C.1.—Construction of the Recombinant Plasmid pGP3.

Plasmid pGP704 (Miller and Mekalanos; J. Bact. 170: 2575-2583 (1988)) was cut simultaneously with restriction enzymes BglII and EcoRI. Using electrophoresis in agarose gel a 3.7 kb DNA fragment was isolated. This fragment incubated in a ligation reaction together with oligonucleotides pGP5' (GAT CGA ATT CAG GAT ATC ACA GAT CT) (SEQ ID NO 3) and pGP3' (ATT TAG ATC TGT GAT ATC GTG AAT TC) (SEQ ID NO 4). The obtained recombinant plasmid was named pGP1.

The pGP1 plasmid was digested with the restriction enzyme PstI. Using electrophoresis in an agarose gel a 3.12 kb DNA fragment was isolated. This fragment was ligated to another fragment of 1.2 kb obtained by digestion of the pUC4K plasmid (Pharmacia) with the restriction enzyme PstI. The so obtained recombinant plasmid was named pGP2.

Using plasmid pMAL-p2 (New England Biolabs) the sequences corresponding to promoter ptac were amplified by PCR using the ptac5' oligonucleotide primers (GAATTC AAT GCT TCT GGC GTC AG) (SEQ ID NO 5) and ptac3' (GGT ACC GGA TGA GAT AAG ATT TTC) (SEQ ID NO 6) which enclose respectively the restriction targets EcoRI and KpnI in its 5' ends. Also from pMAL-p2 plasmid, by PCR the sequences corresponding to the rho-independent terminator of operon rrnB were amplified using the primer oligonucleotides rrnB5' (GGTACC GGA TGA GAT AAG ATT TTC) (SEQ ID NO 7) and rrnB3' (GAATTC AAG AGT TTG TAG AAA CGC) (SEQ ID NO 8) which enclose respectively the restriction targets KpnI and EcoRI in their 5' ends. The size of the DNA amplified fragment comprises 278 base pairs (bp).

With the plasmid pAG408 (Suarez et al; Gene 196: 69-74 (1997)) a fusion of the gene of the GFPUV protein with the region that links to the ribosome of the atpE gene was amplified using the primer oligonucleotides GFP5' (GGTACC TAA TTT ACC AAC ACT AC) (SEQ ID NO 9) and GFP3' (GGTACC TTA TTT GTA GAG CTC ATC) (SEQ ID NO 10) which encloses the restriction target KpnI in its 5' ends. The amplified fragment has a size of 830 bp.

The two first fragments (promoter ptac and terminator rrnB) were digested with the restriction enzymes KpnI and EcoRI whereas that the third (fusion atpE-GFPUV) was digested with the restriction enzyme KpnI. The three fragments obtained in this way were then ligated with the plasmid pGP2 which was previously dephosphorylated and cut with the restriction enzyme EcoRI. Among the different recombinant plasmids obtained one, which was the carrier of the three fragments positioned according to FIG. 2, was chosen. The colonies that carried this plasmid showed an intense fluorescence when exposed to ultraviolet light. The hybrid plasmid so obtained was named pGP3.

C.2—Construction of the Hybrid Plasmid pApxIΔH2.

At this stage, the first objective was to obtain a DNA fragment contiguous to the 5' end of the coding fragment of the second transmembrane helix of apxIA gene. Therefore a fragment of 897 bp was amplified by PCR from the purified geneormic DNA of the App strain HP816 using as primers the ApxIa5' oligonucleotides (GATATC ATG GCT AAC TCT CTC AGC TCG ATA G) (SEQ ID NO 11) and ApxIa3' (CTCGAG GCC TGC CGC CAC ACG TTG) (SEQ ID NO 12), which enclose the restriction targets EcoRV and XhoI in its respective 5' ends. The 7$^{th}$ base of the oligonucleotide ApxIa5' (SEQ ID NO 9) corresponds with the first base of the start codon of the translation of ApxIa gene. The seventh base of oligonucleotide ApxIa3' (SEQ ID NO 10) is complementary to the 885 base of the coding sequence of gene apxIA, being the latter the last base before the initiation of the sequence for the second transmembrane helix.

The second objective of this phase was to obtain a DNA fragment contiguous to the 3' end of the coding segment of the second transmembrane helix of apxIA gene. Therefore, using PCR, a fragment of 1042 bp was amplified from purified genomic DNA of the strain App HP816 using as primers the oligonucleotides ApxIb5' (CTCGAG CCG CTT TCG TTC TTA AAT GTT GCG) (SEQ ID NO 13) and ApxIb3' (AGATCT TCA CCG GCT TTC TGT GCA CTT TG) (SEQ ID NO 14) which include the restriction targets XhoI and BglII in its respective 5' ends. The 7$^{th}$ base of oligonucleotide ApxIb5' (SEQ ID NO 13) corresponds with the base 946 of the coding sequence of the apxIA gene, being this one the first base after the end of the sequence for the second transmembrane helix. The seventh base of oligonucleotide ApxIb3' (SEQ ID NO 14) is complementary to base 1975 of the coding sequence of the gene apxIA.

Once the two fragments previously described have were obtained, the first one was digested with the restriction enzymes EcoRV and XhoI, whereas that the second was digested with the enzymes XhoI and BglII. Both fragments were then ligated with vector pGP3 which was previously cut with the restriction enzymes EcoRV and BglII. The resulting hybrid plasmid was named pApxIΔH2.

C.3.—Construction of the Hybrid Plasmid pApxIIΔH2.

The first objective, at this stage, was to obtain a DNA fragment contiguous to the 5' end of the coding segment of the second transmembrane helix of gene apxIIA. Therefore, by PCR, a 871 bp fragment was amplified from the purified genomic DNA of the App strain HP816 using as primers the oligonucleotides ApxIIa5' (GATATC AAA TCG TCC TTA CAA CAA GGA TTG) (SEQ ID NO 15) and ApxIIa3' (GAATTC ACC TGA AGC GAC TCG TTG GGC) (SEQ ID NO 16) which enclose the restriction targets EcoRV and EcoRI in its 5' respective ends. The number 7 base of oligonucleotide ApxIIa5' (SEQ ID NO 15) corresponds to base 27 of the coding sequence of the gene apxIIA. The seventh base of oligonucleotide ApxIIa3' (SEQ ID NO 16) is complementary to the base 885 of the coding sequence of gene apxIIA, being this one the last base before the start of the sequence for the second transmembrane helix.

The second objective of this step, was to obtain a DNA fragment contiguous to the 3' end of the coding segment of the second transmembrane helix of apxIIA gene. Therefore a 952 bp fragment was amplified by PCR from the purified genomic DNA from the App strain HP816 using as primers the oligonucleotides ApxIIb5' (GAATTC CCT CTT TCA TTC TTA AAT GTA GC) (SEQ ID NO 17) and ApxIIb3' (AGATCT GCC ATC AAT AAC GGT AGT ACT TG) (SEQ ID NO 18), which enclose the restriction targets EcoI and BglII at its 5' respective ends. The 7$^{th}$ base of oligonucleotide ApxIIb5' (SEQ ID NO 17) matches up with the base 946 of the coding sequence of gene apxIIA, being the latter the first base after the end of the sequence for the second transmembrane helix. The seventh base of the oligonucleotide ApxIIb3' (SEQ ID NO 18) is complementary to the base 1845 of the coding sequence of the apxIIA gene.

Once the two fragments described previously were obtained, the first one was digested with the restriction enzymes EcoRV and EcoRI whereas that the second one was digested with the enzymes EcoRI and BglII. Both fragments were then ligated with the vector pGP3 previously digested with the restriction enzymes EcoRV and BglII. The resulting hybrid plasmid was named pApxIIΔH2.

D.—Construction of the Recombinant Bacteria which have Resolved the Hybrid Plasmid Inserted in the Genome.

D.1. Construction of the App Recombinant Strain HP816R1.

The transformation of App with the hybrid plasmid pApxIΔH2 was done by conjugation from the *E. coli* S17-1 λ pir cells which are carriers of this plasmid. The strain HP816N1$^r$ was used for the transformation with the hybrid plasmid pApxIΔH2.

Before carrying out the conjugation, a culture in stationary phase was obtained for such bacteria. The culture medium TSYN (SoyaTryptic broth 30 g/L, yeast extract 6 g/L and once autoclaved supplemented with 0.004% NAD) and nalidixc acid (50 μg/mL) was used for the growth of App816N1$^r$.

The culture medium LB (Tryptone 10 g/L, yeast extract 5 g/L, NaCl 10 g/L) that once autoclaved was supplemented with 25 μg/mL of kanamycin was used to grow *E. coli* S17-1 λ pir. Once the stationary phase was achieved, 0.2-0.3 $A_{600}$ units of the App culture and 0.6-0.8 $A_{600}$ units of the *E. coli* culture were added to 1 mL of a 10 mM solution of $MgSO_4$. Next it was centrifuged during 2 minutes at 15,000 g and the pellet so obtained was resuspended in 200 μl of a 10 mM $MgSO_4$ solution. Once the mixture of both cultures had been done, this was extended on a 2.5 cm and 0.45 μM nitrocellulose filter previously placed on a Petri dish containing TSYN medium supplemented with 15 g/L Noble agar. After incubation during 6 hours at 37 C., the filter with the conjugation was placed in a tube containing 2 mL of PBS ($Na_2HPO_4$ 10 mM, $KH_2PO_4$ 1 mM, NaCl 137 mM, KCl 2 mM pH 7.4). After vigorous shaking, the filter was removed and the cell suspension was centrifuged during 2 minutes at 15,000 g and the pellet was resuspended in 500 μL of PBS. The so obtained suspension was distributed in Petri dishes with TSYN medium supplemented with 15 g/L Noble Agar, 50 μg/mL kanamycin and 50 μg/mL nalidixic acid, at a rate of 100 μL of cell suspension for each Petri dish. The resulting cultures were incubated at 37 C. for 24-36 hours. With this procedure 65 colonies resistant to kanamicin and nalidixic acid, were obtained for the conjugation with the plasmid pApxIΔH2, which equals a frequency of transformation of $1.3 \times 10^{-7}$ for each receptor cell.

Several colonies were reseeded by exhaustion of the loop in Petri dishes containing LP supplemented with 15 g/L Noble Agar, 0.004% NAD, 50 μg/mL kanamycin and 50 μg/mL nalidixic acid. All the resulting colonies exhibited distinct degrees of fluorescence when exposed to ultraviolet light, which indicated the integration of the plasmid in the App genome in a unique recombination event. As shown in FIG. 3, if a double recombination took place, the exconjugates would be unable to grow in a kanamycin containing medium. The presence of this antibiotic in the plates allows only the growth of those recombinants that have integrated the entire plasmid in its genome. The indicator gene GFP allows to discriminate if any of the colonies which are resistant to the kanamycin is the product of a spontaneous mutation.

Finally, the obtained recombinants were originated from a homologous recombination between a plasmid and the apxIA gene. This was verified by observing the haemolytic activity of the recombinants in Columbia blood agar plates supplemented with 0.004% NAD (FIG. 3, panel C) The recombinants obtained with plasmid pApxIΔH2 exhibit a sharp decrease of the diameter of the haemolytic halo compared to the parent strain HP816N1$^r$.

One of the recombinants obtained with the plasmid pApx-IΔH2 was selected for the later passages and was referred to as HP816R1.

D.2 Construction of the Strain AppApxIH2$^-$

Once the recombinants with the plasmid pApxIΔH2 integrated in the genome have been obtained, it is essential to fix the deletion in the App genome by means of a second recombination. Therefore one of the recombinants of the previous stage was submitted to serial passages in a culture medium supplemented only with nalidixic acid. A medium without kanamicin allows that, in case that a second recombination between the App genome and the integrated plasmid occurs, the resulting bacteria be viable. This second recombination event gives rise to the appearance of two different genotypes. In case that this occurs in the same segment in which the first recombination took place, the resulting genotype will be identical to the parent strain used in section D.1. If this second recombination occurs in the segment where the first recombination did not take place, the resulting genotype will show a deletion in the fragment that codes for the second transmembrane helix of the haemolysin FIG. 3, panel A). The appearance off recombinants may be monitored in several different ways: a) disappearance of the fluorescence when the colonies are exposed with ultraviolet light; b) sensibility to kanamicin and c) recovery of the haemolytic halo exhibited by the parental strain used in section D.1. Methods a) and b) detect both recombinant types. Method c) makes possible to distinguish those recombinants which recover the parental geneotype. This is due to the fact that the recombinants which show the deletion in the coding segment of the second transmembrane helix of the apxIA gene, the haemolytic activity of the corresponding parental phenotype is not re-established.

The serial passages were performed from previous passages using 1/10000 dilutions of the previous passage, with the exception of the first passage which simply consisted of a culture obtained from a colony isolated from HP816R1. The culture medium was LB supplemented with 0.004% NAD and 50 μg/nL of nalidixic acid. For each passage a volume of 10 mL of medium was used. The percentages of detected recombinants are shown in table 1

TABLE 1

| Passage Number | % detected recombinants (a) | % detected recombinants (b) |
| --- | --- | --- |
| 2 | 0.12% | 0.18% |
| 3 | 0.32% | 0.46% |
| 4 | 7.75% | 10.4% |
| 5 | 18.5% | 22.3% | a) percentage determined by colony counting which recovered the haemolytic halo which was exhibited by the parent strain.
b) percentage determined by counting the colonies that did not show fluorescence when exposed to ultraviolet light.

As observed in the table above, in each passage the number of bacteria that show a resolved plasmid due to a second recombination increases. The percentage of non-fluorescent colonies is only slightly higher than that of the colonies that recover the haemolytic activity. This fact suggests that the second recombination occurs preferably in the same DNA segment where the first recombination occurred. If the frequency for each recombinat type were of 50%, double the number of non-fluorescent colonies with respect to those that recover the haemolytic activity.

Once the culture has been sufficiently enriched in second recombinants, the purification step can be initiated. With this aim in mind, several non-fluorescent colonies were propagated in Columbia agar supplemented with NAD and LB agar supplemented with NAD, 50 μg/mL, nalidixic acid and 20 μg/mL kanamicin (LBNKm). For later studies, several colonies were chosen that did not show growth on LBNKm and that showed the same haemolytic activity that the recombinant by insertion HP816R1.

D.3—Construction of the App HP816R2 Recombinant Strain.

The transformation of the App with the pApxIIΔH2$^-$ was performed by conjugation from the *E. coli* S17-1 λ pir which are the carriers of these plasmids. The strain AppApxIH2$^-$ was used for the transformation with the hybrid plasmid pApxIIΔH2. The procedures and the culture media are identical to those described in section D.1. The transformation frequency with the plasmid pApxIIΔH2 was similar to that obtained is section D.1. for plasmid pApxIΔH2.

Several colonies were reseeded by exhaustion of the loop in Petri dishes with LB supplemented with 15 g/L Noble agar 0.004% NAD, 50 μg/mL kanamicin and 50 μg/mL nalidixic acid. All resulting colonies exhibited distinct degrees of fluorescence when exposed with ultraviolet light, which indicates the integration of the plasmid in the App genome in a single recombination event. As observed in FIG. 4, if a double recombination occurs, the exconjugates will be unable to grow in a kanamicin containing medium. The presence of this antibiotic in the plates allows only the growth of those recombinants which have integrated in its genome the entire plasmid. The indicator gene GFP allows to discriminate if any of the colonies, which are resistant to kanamicin, is the product of a spontaneous mutation.

Finally the obtained recombinants were originated from a homologous recombination between the plasmid and the apxIIA respective gene. This was proved by observing the haemolytic activity of the recombinants in Columbia agar plates supplemented with 0.004% NAD (FIG. 4, panel C). The recombinants obtained with the plasmid pApxIIH2 show a complete disappearance of the haemolytic halo.

One of the recombinants obtained with the plasmid pApxI-IΔH2 was chosen for later passages and named HP816R2.

D.4 Construction of the AppApxI/IIH2$^-$ Strain.

Once the recombinants had been obtained with plasmid pApxIIΔH2 integrated in the genome it was essential to fix the deletion in the App genome by means of a second recombination. Therefore the recombinants obtained in the previous stage were submitted to serial passages in culture medium supplemented only with nalidixic acid as described in D.2. The values of the percentages of recombinants detected from the second passage, are similar to those obtained in D.2.

Once the culture is sufficiently enriched in secondary recombinants, the purification stage can proceed. With this aim in mind, several non-fluorescent colonies were multiplied in Columbia agar supplemented with NAD and LB agar supplemented with NAD, 50 μg/mL nalidixic acid and kanamicin 20 μg/mL (LBNKm). For later studies several colonies were chosen which did not show growth on LBNKm and showed the same haemolytic activity than the recombinant by insertion HP816R2.

E.—Analysis of the DNA Purified from the colonies, isolated in the previous passage, to test the homogeneity of the cultures and the presence of the deletion in genes apxIA and apxIIA.

The recombinants of the previous passages D.2 and D.4 were grown in 10 mL of TSYN medium supplemented with 50 µg/mL nalidixic acid until the stationary phase was reached. Later the DNA extraction of each one of them was performed.

E.1.—Analysis of the apxIH2⁻ Recombinants.

The samples of the genomic DNA corresponding to each one of the cultures of the second recombinants obtained from plasmid pApxIΔH2 were digested with the restriction enzyme XhoI. These digestions, together with others performed from the DNA extracted from the cultures of the strain HP816N1$^r$ and HPB816R1 respectively, were analysed by Southern-blot using the fragment of DNA of 1927 bp coming from the digestion of plasmid pΔApx1H2⁻ with the restriction enzymes EcoRV and BglII as probe. The results of these hybridisations are shown in FIG. 3B. The results of the hybridisation of the control strain HP$_{816}$N1$^r$ show the presence of a restriction; target XhoI placed at approximately 20 kb of that found within operon apxI. The analysis of the recombinant with the insertion of plasmid pApxIΔH2, shows the appearance of two new bands of 1.1 and 4.3 kb and a slight increase of approximately 1 kb of the preexisting band of 20 kb. The size of the new bands and the increase of the preexisting one, are the expected from the insertion of the hybrid plasmid pApxΔH2 in the 5' flanking region of the coding fragment of the second transmembrane helix of the apxIA gene of the App genome (FIG. 3A, outline 2). The analysis of the recombinant with the plasmid resolved from the second recombination in the same 5' region where the first took place, show the disappearance of the two bands of lesser molecular mass and a slight decrease of the mobility of the previous 21 kb band which now appears at the same level as the parent strain. This, together with the fact hat the haemolytic activity is identical to that exhibited by the parent strain HP816N1$^r$, suggests that no additional modifications are introduced in the App genome during all this process (FIG. 3, A, and C).

Finally, the analysis of the recombinant with the plasmid resolved from a second recombination in the 3' flanking region of the segment that codes the second transmembrane helix shows the disappearance of the 4.3 kb band, the maintenance of the 1.1 kb band which was already observed in the recombinant by insertion and a slight decrease of the 20 kb band. This bands distribution is the expected one, due to the disappearance of the coding segment of the second transmembrane helix and its substitution by a XhoI target. This new target, inserted in the App genome, gives rise to the 1.1 kb fragment and the consecutive decrease of 1.1 kb in the 20 kb band which is observed in the strain 816 N1$^r$ (FIGS. 3A and B). Note in CA the presence of large haemolytic halos surrounding the colonies of cultures 1 and 3 and of small haemolytic halos surrounding the colonies of cultures 2, 4 and 5. See also the absence of growth in TS of the cultures 1, 3, 4 and 5. This recombinant shows a very reduced haemolytic activity as compared to the parent strain HP816 N1$^r$ and the same haemolytic activity than a serotype 7 App which possesses only the ApxII haemolysin (FIG. 3C). This result indicates that the deletion in the second transmembrane helix eliminates or reduces considerably the haemolytic activity of the App ApxIA. The App modified by the described deletion will be named, from now on, ApxIAH2$^-$.

The recombinant so obtained, characterized by having a deletion in nucleotides 886 to 945 in the apxIA gene which code the second transmembrane domain of the ApxI exotoxin, has been named AppApxIH2$^-$. On the 10$^{th}$ Jan. 2002 this has been deposited in the Colección Española de Cultivos Tipo with the registration number CECT 5985, according to the conditions established in the Budapest treaty.

E.2.—Analysis of the apx/IIH2⁻ Recombinants.

The genomic DNA samples corresponding to the recombinant by insertion HP816R2 and to the second recombinants obtained from the plasmid pApxIIΔH2$^-$ were digested with the restriction enzyme EcoRI. These digestions together with another one performed from a DNA extracted from a culture of the strain HP816N1$^r$, were analysed using the Southern-blot. As a probe, the two DNA fragments amplified by PCR were used. These corresponded to the 5' and 3' flanking regions of the DNA segment that codes for the second transmembrane helix of the ApxII (Section B). The results of these hybridisations are shown in FIG. 4B. The results of the hybridisation of the control strain HP816 N1$^r$ show the presence of two EcoRI restriction targets distant from one another 15.7 kb, which delimit a fragment in which operon apxII is enclosed. The analysis of the recombinant by insertion of plasmid pApxIIΔH2 shows the disappearance of the 15.7 kb band and the appearance of 3 new bands of 8.2, 7.5, and 0.9 kb. The size of the new bands is the expected from the insertion of the hybrid plasmid pApxIIΔH2 in the 3' flanking region of the coding segment of the second transmembrane helix of gene apxIIA of the App genome (FIG. 4A). The analysis of the recombinant with the resolved plasmid from the second recombination in the same 3' region where it took place the first one, shows the reappearance of a single 15.7 kb band which coincides with that shown by the control strain (FIG. 4B). The haemolytic activity is identical to the one shown by the AppApxIH2$^-$ parent strain (FIG. 4C). Finally, the analysis of the recombinant with the plasmid resolved from a second recombination by the 3' flanking region of the segment that codes the second transmembrane helix shows the disappearance of the 13.5 and 0.9 kb bands and the appearance of a new 7.5 kb fragment (FIG. 4B). This band distribution is the expected one, from the disappearance of the coding segment of the second transmembrane helix and its substitution by an EcoRI target (FIG. 4A). This new target inserted in the App genome causes the 15.7 kb EcoRI, fragment, which included operon apxII in the parent strain, to split in two 8.2 and 7.5 kb fragments (FIGS. 4A and B). This recombinant is virtually non-haemolytic (FIG. 4C). This result indicates that the deletion in the second transmembrane wipes out or reduces in its practical entirety, the haemolytic activity of the App ApxIIA. The ApxIIA modified by carrying out the described deletion will be renamed from now on as ApxIIAH2$^-$. Notice in CA the presence of small haemolytic halos surrounding the colonies of cultures 1 and 3 and the absence of haemolytic halos surrounding the colonies of cultures 2 and 4. Notice also the absence of growth of cultures 1, 3 and 4 in TS.

The recombinant strain so obtained has been renamed AppApxI/IIH2⁻. This is characterized by having a deletion in nucleotides 886 to 945 in the ApxIA gene which code a second transmembrane domain of the ApxI exotoxin and furthermore a deletion of nucleotides 886 to 945 of the apxIIA gene which codes the second transmembrane domain of the ApxII exotoxin. This strain has been deposited in the Colección Española de Cultivos Tipo, on the 12$^{th}$ Jun. 2002 with the registration number CECT 5994 as specified in the conditions of the Budapest Treaty on patents.

F.—Analysis of the Production of the ApxIAH2⁻ and ApxIIAH2⁻ by the Recombinants Strains Obtained.

Figure 6:
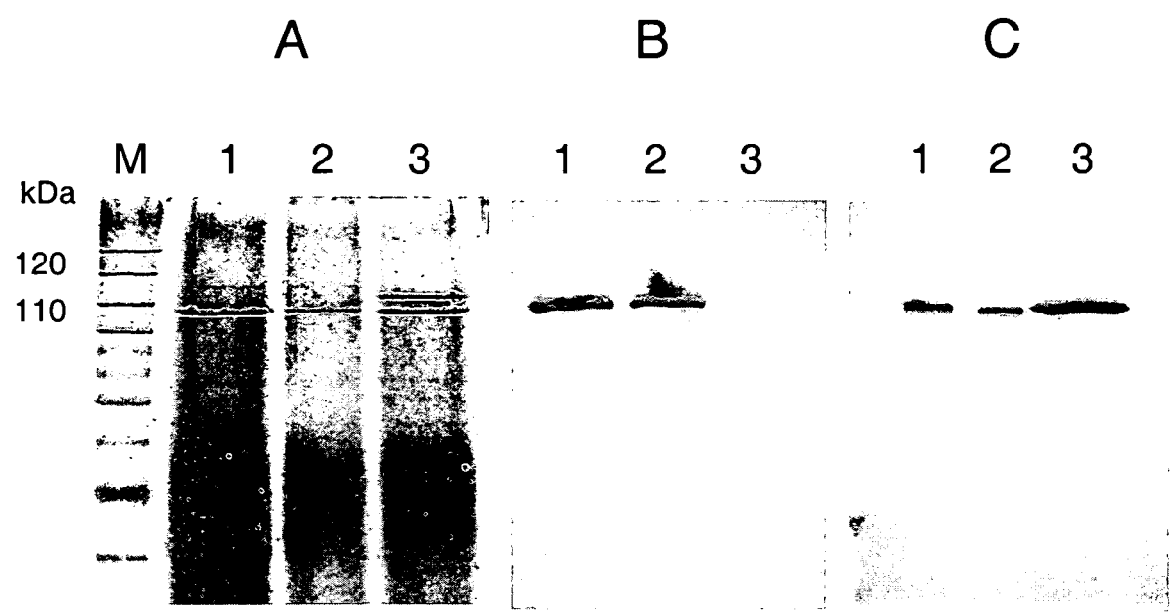

To determine if the obtained recombinant strains were still producing the ApxH2⁻ the concentration of the same in the LB medium was determined. The Apx produced were detected using monoclonal antibodies specific to the Apx I and Apx II using immunoassays and Western-blot. As shown in FIG. 5 (A and B) the production and excretion to the medium of the ApxIAH2⁻and ApxIIAH2⁻ by the recombinant strains follows the same temporary patter than the non-modified Apx from the parent wild type strain HP816N1$^r$. All haemolysins (modified or not) appear in the culture medium at about the second half of the exponential growth phase and reach the maximum concentration at the beginning of the stationary phase. From this moment onward, the concentration of all haemolysin remains stable or decreases slightly. As observed in the same figure, ApxIAH2⁻ and ApxIIAH2⁻ accumulate until reaching levels similar to those shown in the respective non-modified Apx produced by the wild type parent strain HP816N1$^r$. On the other hand, the introduced deletion is very small (18 amino-acids) and only a decrease of 2 kD in the molecular mass of the two ApxH2⁻ is expected. Bearing in mind that the 2 wild type haemolysins have an apparent molecular mass of approximately 105 kDa, a decrease of 2 kDa in its molecular mass is unnoticeable in the polyacrilamide gels and its corresponding Western-blots (FIG. 6). Finally, we must highlight that in this same figure do not appear, truncated or improperly processed polypeptidic products. Notice that the 105 kDa in track 3 appears detected only in (C). All these data indicate that the small deletion introduced in both Apx does not hinder that these be synthesized in a full way and exported to the culture medium. Once these have been freed in the culture medium, the ApxH2⁻ exhibit a stability similar to that shown by the respective non-modified Apx.

G.—Effectiveness of the Attenuation of the Obtained Strains.

To test the degree of attenuation of the two constructed recombinant strains, three months old, male and female LW×LD hybrid swine, were used. Four replicates of swine were used in the different trials. Each one of the strains was administered at a dose of $10^8$ cfu in 5 mL of PBS, to each one of the animals of the 3 first groups, by intratracheal injection. Previously this dose was determined as the LD50 for the wild type strain HP816N1$^r$ in swine of this age. The animals of the fourth group were inoculated only with one dose of 5 mL of PBS The clinical signs were noted down daily during the 7 days period that lasted the trial. The results are shown in table 2:

TABLE 2

| Strain | Number of Animals | Dosage App (cfu) | Mortality | Days with behaviour disturbances | | | Days with clinical respiratory signs (b) | | |
|---|---|---|---|---|---|---|---|---|---|
| | | | | 0-2 | 3-4 | 5-6 | 0-2 | 3-4 | 5-6 |
| HP816Nl$^r$ | 5 | $10^8$ | 2/5 | 5/5 | 3/3 | 3/3 | 5/5 | 1/3 | 0/3 |
| AppApxIH2⁻ | 10 | $10^8$ | 0 | 10/10 | 9/10 | 4/10 | 5/10 | 3/10 | 3/10 |
| AppApxI/IIH2⁻ | 10 | $10^8$ | 0 | 4/10 | 0/10 | 0/10 | 2/10 | 0/10 | 0/10 |
| Control (PBS) | 5 | N.A. | 0 | 0/5 | 0/5 | 0/5 | 0/5 | 0/5 | 0/5 |

(a) Animals with impaired alert behaviour and ability to respond in the presence of the caretaker (Affected/total)
(b) Animals with disturbed respiratory rhythm and/or dyspnea (Affected/Totals).

Seven days after the inoculation the animals were sacrificed and the observed macroscopic lesions, in the respiratory organs, were recorded. Bacteriological examinations were also carried out at the necropsy.

The results obtained in this trial are summarized in Table 3

TABLE 3

| Strain | Number of animals | Dosage App (cfu) | Mortality | Animals with lung lesions | Mean lung lesion Index | Animals from which App was isolated |
|---|---|---|---|---|---|---|
| HP816Nl$^r$ | 5 | $10^8$ | 2/5 | 4 | 11.6 ± 2.1 | 3 |
| AppApxIH2⁻ | 10 | $10^8$ | 0 | 7 | 3.2 ± 4.6 | 3 |
| AppApxI/IIH2⁻ | 10 | $10^8$ | 0 | 0 | 0 | 8 |
| Control (PBS) | 5 | N.A. | 0 | 0 | 0 | 0 |

Two out of 5 animals of this group died during this period of time. At the necropsy, four out of five animals, showed severe lung lesions. The animals which had been inoculated with the strain AppApxIH2⁻ showed also a modification of their behaviour, although these signs slowed down from the forth inoculation day. The clinical signs were milder and were only observed in 50% of the pigs. Although none of the animals of this group died during the trial, 70% of them showed lesions at the necropsy although all of them were found to be milder than the previous group. The third group was inoculated with the strain AppApx/IIH2⁻. Although four of the animals showed mild modified behaviour, these slowed down from the 48$^{th}$ hour post-inoculation. The two animals that showed limited clinical signs also recovered within 48 hours after the inoculation. No lung lesions were observed in none of the animals at the necropsy. The assessment of the lung lesions was done according to Hannan et al; (Research in Veterinary Science 33:76-88 (1982)). The values shown are the arithmetical means of each group together with the standard deviation. According to these results, the AppApxI/IIH2⁻ strain is non-virulent and can be used safely as a live vaccine. It is important to highlight that the App strain inoculated was recovered in 80% of the pigs of this group, seven days after its administration. This result indicates that the viability of the AppApxI/IIH2⁻ strain in an experimental infection is not modified in spite of the fact that it is devoid of haemolytic activity. This fact is important if we bear in mind that it is essential that the microorganism remains viable so that the Apx exotoxins can be generated and freed. Without the production of the Apx exotoxins, the attenuated strain could not be used as live vaccine since this would be unable to induce an immune response which would protect the animal against future infections (Reimer et al; Microbial Pathogenesis 18:197-209 (1995)). In all trials a strong immunogenic response has been achieved.

The invention claimed is:

1. An isolated immunogenic, non-haemolytic *Actinobacillus pleuropneumoniae* (App) strain comprising at least one mutation in a transmembrane domain-encoding segment of the apxIA gene wherein the segment of the apxIA gene corresponds to nucleotides 886 to 945, nucleotides 697 to 759, or nucleotides 1105 to 1215 of SEQ ID NO. 1, and with or without at least one mutation in a transmembrane domain-encoding segment of the apxIIA gene, wherein the segment of the apxIIA gene corresponds to nucleotides 886 to 945, nucleotides 697 to 759, or nucleotides 1105 to 1215 of SEQ ID NO. 2.

2. The strain of claim 1, wherein said mutation is a deletion.

3. The strain of claim 2, wherein said deletion is in a region of the apxIA gene which encodes a second transmembrane domain of the App ApxI exotoxin.

4. The strain of claim 3, wherein said deletion is of nucleotides 886 to 945 of SEQ ID NO. 1.

5. The strain of claim 4, wherein, said strain additionally comprises a deletion in a region of the apxIIA gene which encodes a second transmembrane domain of the App ApxII exotoxin.

6. The strain of claim 5, wherein said deletion is of nucleotides 886 to 945 of SEQ ID NO. 2.

7. A vaccine composition against porcine pleuropneumonia comprising an immunogenically effective amount of the *Actinobacillus pleuropneumoniae* strain of claim 1, and a pharmaceutically acceptable carrier, wherein the porcine pleuropneumoniae is caused by *Actinobacillus pleuropneumoniae*.

8. A method for obtaining an immunogenic, non-haemolytic Actinobacillius pleuropneumoniae (App) strain comprising introducing at least one mutation in a transmembrane domain-encoding segment of the apxIA gene, wherein the segment of the apxIA gene corresponds to nucleotides 886 to 945, nucleotides 697 to 759, or nucleotides 1105 to 1215 of SEQ ID NO. 1, and with or without at least one mutation in a transmembrane domain-encoding segment of the apxIIA gene wherein the segment of the apxIIA gene corresponds to nucleotides 886 to 945, nucleotides 697 to 759, or nucleotides 1105 to 1215 of SEQ ID NO. 2.

9. The method of claim 8, wherein said mutation is a deletion.

10. The method of claim 9, wherein said deletion is in a region of the apxIA gene which encodes a second transmembrane domain of the App ApxI exotoxin.

11. The method of claim 10, wherein said deletion is of nucleotides 886 to 945 of SEQ ID NO. 1.

12. The method of claim 11, wherein said method additionally comprises introducing a deletion in a region of the apxIIA gene which encodes a second transmembrane domain of the App ApxII exotoxin.

13. The method of claim 12, wherein said deletion is of nucleotides 886 to 945 of the SEQ ID NO. 2.

14. An immunogenic and non-haemolytic strain of *Actinobacillus pleuropneumonia* having the characteristics of that deposited in the Colección Española de Cultivos Tipo under registration number CECT 5985, or a mutant thereof.

15. A vaccine composition against porcine pleuropneumoniae comprising an immunogenically effective amount of the *Actinobacillus pleuropmeumoniae* of claim 14; and a pharmaceutically acceptable carrier.

16. An immunogenic and non-haemolytic strain of *Actinobacillus pleuropneumoniae* having the characteristics of that deposited in the Colección Española de Cultivos Tipo under registration number CECT 5994, or a mutant thereof.

17. A vaccine composition against porcine pleuropneumonia comprising an immunogenically effective amount of the *Actinobacillus pleuropneumoniae* of claim 16, and a pharmaceutically acceptable carrier.

* * * * *

SEQUENCE LISTING

<160> NUMBER OF SEQ ID NOS: 18

<210> SEQ ID NO 1
<211> LENGTH: 3072
<212> TYPE: DNA
<213> ORGANISM: Actinobacillus pleuropneumoniae

<400> SEQUENCE: 1

```
atggctaact ctcagctcga tagagtcaaa ggattgattg attcacttaa tcaacataca        60
aaaagtgcag ctaaatcagg tgccggcgca ttaaaaaatg gtttgggaca ggtgaagcaa       120
gcagggcaga aattaatttt atatattccg aaagattatc aagctagtac cggctcaagt       180
cttaatgatt tagtgaaagc ggcggaggct ttagggatcg aagtacatcg ctcggaaaaa       240
aacggtaccg cactagcgaa agaattattc ggtacaacga aaaaactatt aggtttctcg       300
gaacgaggca tcgcattatt tgcacctcag tttgataagt tactgaataa gaaccaaaaa       360
ttaagtaaat cgctcggcgg ttcatcggaa gcattaggac aacgtttaaa taaaacgcaa       420
acggcacttt cagccttaca aagtttctta ggtacggcta ttgcgggtat ggatcttgat       480
agcctgcttc gtcgccgtag aaacggtgag gacgtcagtg gttcggaatt agctaaagca       540
ggtgtggatc tagccgctca gttagtggat aacattgcaa gtgcaacggg tacggtggat       600
gcgtttgccg aacaattagg taaattggca atgccttatc taacactcgc cttaagcggt       660
ttagcaagta agttaaataa ccttccagat ttaagccttg caggacctgg gtttgatgcc       720
gtatcaggta tcttatctgt tgtttcggct tcattcattt taagtaataa agatgccgat       780
gcaggtacaa aagcggcggc aggtattgaa atctcaacta aaatcttagg caatatcggt       840
aaagcggttt ctcaatatat tattgcgcaa cgtgtggcgg caggcttatc cacaactgcg       900
gcaaccggtg gtttaatcgg ttcggtcgta gcattagcga ttagcccgct ttcgttctta       960
aatgttgcgg ataagtttga acgtgcgaaa cagcttgaac aatattcgga gcgctttaaa      1020
aagttcggtt atgaaggtga tagtttatta gcttcattct accgtgaaac cggtgcgatt      1080
gaagcggcat taaccacgat taacagtgtg ttaagtcgcg gttccgcagg tgttggggct      1140
gctgcaaccg gctcattagt cggtgcgccg gtagcagctt tagttagtgc aatcaccggt      1200
attatttcag gtattttaga tgcttctaaa caggcaatct cgaacgagt tgcaacgaaa       1260 ttagcgaata agattgacga atgggagaaa aaacacggta aaaactattt tgaaaacggt      1320
```

```
tatgacgccc gccattccgc attcttagaa gatacctttg aattgttatc acaatacaat    1380
aaagagtatt cggtagagcg tgtcgttgct attacgcaac agcgttggga tgtcaatatc    1440
ggtgaacttg ccggcattac tcgcaaaggt tctgatacga aaagcggtaa agcttacgtt    1500
gatttctttg aagaaggaaa acttttagag aaagaaccgg atcgttttga taaaaaagtg    1560
tttgatccgc ttgaaggtaa aatcgacctt tcttcaatta acaaaaccac tttattgaaa    1620
tttgttacgc cggtctttac cgcaggtgaa gagattcgtg agcgtaagca aaccggtaaa    1680
taccaatata tgaccgaatt attcgttaaa ggtaaagaaa aatgggtggt aaccggtgtg    1740
cagtcacata atgcgattta tgactatacg aatcttatcc aattagcgat agataaaaaa    1800
ggtgaaaaac gtcaagtgac cattgaatct catttgggtg agaaaaatga tcgtatatat    1860 cttcatccg gttcatctat cgtatatgcg ggtaacggac atgatgtagc atattacgat    1920
aaaaccgata caggttactt aacatttgac ggacaaagtg cacagaaagc cggtgaatat    1980
attgtcacta agaacttaa agctgatgta aaagttttaa aagaagtggt taaaactcag    2040
gatatttcag ttggaaaaac gtgcagtgaa aaattagaat atcgtgatta tgagttaagc    2100
ccattcgaac ttgggaacgg tatcagagct aaagatgaat tacattctgt tgaagaaatt    2160
atcggtagta atcgtaaaga caaattcttt ggtagtcgct ttaccgatat tttccatggt    2220
gcgaaaggcg atgatgaaat ctacggtaat gacggccacg atatcttata cggagacgac    2280
ggtaatgatg taatccatgg cggtgacggt aacgaccatc ttgttggtgg taacggaaac    2340
gaccgattaa tcggcggaaa aggtaataat ttccttaatg gcggtgatgg tgacgatgag    2400
ttgcaggtct ttgagggtca atacaacgta ttattaggtg gtgcgggtaa tgacattctg    2460
tatggcagcg atggtactaa cttatttgac ggtggtgtag gcaatgacaa aatctacggt    2520
ggtttaggta aggatattta tcgctacagt aaggagtacg gtcgtcatat cattattgag    2580
aaaggcggtg atgatgatac gttattgtta tcggatctta gttttaaaga tgtaggattt    2640
atcagaatcg gtgatgatct tcttgtgaat aaaagaatcg gaggaacact gtattaccat    2700
gaagattaca atgggaatgc gctcacgatt aaagattggt tcaaggaagg taagaagga    2760 caaaataata aaattgaaaa aatcgttgat aaagatggag cttatgtttt aagccaatat    2820
ctgactgaac tgcagctcc tggaagaggt atcaattact ttaatgggtt agaagaaaaa    2880
ttgtattatg gagaaggata taatgcactt cctcaactca gaaagatat tgaacaaatc    2940 atttcatcta cgggtgcatt taccggtgat cacggaaaag tatctgtagg ctcaggcgga    3000
ccgttagtct ataataactc agctaacaat gtagcaaatt ctttgagtta ttcctttagca   3060 caagcagctt aa                                                         3072

<210> SEQ ID NO 2
<211> LENGTH: 2871
<212> TYPE: DNA
<213> ORGANISM: Actinobacillus pleuropneumoniae

<400> SEQUENCE: 2
atgtcaaaaa tcactttgtc atcattaaaa tcgtccttac aacaaggatt gaaaaatggg       60
aaaaacaagt taaatcaagc aggtacaaca ctgaagaatg gtttaactca aactggtcat      120
tctctacaga atggggctaa aaaattaatc ttatatattc ctcaaggcta tgattcgggt      180
caaggaaatg gagttcaaga tttagttaaa gctgctaatg atttaggtat tgaagtatgg      240
cgagaagaac gcagcaattt ggacattgca aaaactagct ttgatacaac tcagaaaatt      300
```

```
ctaggtttta ctgatagagg aattgtatta tttgcacctc agctagataa tttattaaag    360
aagaatccta aaattggcaa tacattagga agtgcttcta gcatctcaca aaatataggt    420
aaagccaata ctgtattagg tggtattcaa tctattttag gatctgtttt atctggagta    480
aatctgaatg aattacttca aaataaagat cctaatcaat tagaacttgc aaaagcaggg    540
ctagaactga ctaatgaatt agttggtaat attgctagct cggtgcaaac tgtagatgca    600
tttgcagaac aaatatctaa actaggttca catttacaga atgtgaaagg attaggagga    660
ttgagtaata aattacaaaa tctaccagat ctaggaaaag caagtttagg tttggacatt    720
atctctggtt tactttctgg agcatctgca ggtctcattt tagcagataa agaggcttca    780
acagaaaaga aagctgccgc aggtgtagaa tttgctaacc aaattatagg taatgtaaca    840
aaagcggtct catcttacat tcttgcccaa cgagtcgctt caggtttgtc ttcaactggt    900
cctgtcgctg cattaatcgc atctacagtt gcactagctg ttagccctct ttcattctta    960
aatgtagctg ataagtttaa acaagctgat ttaatcaaat catattctga acgcttccaa   1020
aaattaggat atgatggaga tcgtttatta gctgattttc accgtgagac aggaactatt   1080
gatgcttctg taacaacaat taacactgct ttagcagcta tctccggtgg agttggagct   1140
gcaagcgcgg ttctctagt cggagctcca gttgcgttac tcgttgctgg tgttacggga   1200
cttattacaa ctattctaga atattctaaa caagccatgt ttgaacatgt tgcaaataag   1260
gttcatgaca gaatagttga atgggagaaa aaacataata aaaactattt tgagcaaggt   1320
tatgattctc gtcatttagc tgatttacaa gacaatatga agtttcttat caatttaaat   1380
aaagaacttc aggctgaacg cgtagtagct attacccaac aaagatggga taaccaaatt   1440
ggagacctag cggcaattag ccgtagaacg gataaaattt ccagtggaaa agcttatgtg   1500
gatgcttttg aggaggggca acaccagtcc tacgattcat ccgtacagct agataacaaa   1560
aacggtatta ttaatattag taatacaaat agaaagacac aaagtgtttt attcagaact   1620
ccattactaa ctccaggtga agagaatcgg gaacgtattc aggaaggtaa aaattcttat   1680
attacaaaat tacatataca aagagttgac agttggactg taacagatgg tgatgctagc   1740
tcaagcgtag atttcactaa tgtagtacaa cgaatcgctg tgaaatttga tgatgcaggt   1800
aacattatag aatctaaaga tactaaaatt atcgcaaatt taggtgctgg taacgataat   1860
gtatttgttg ggtcaagtac taccgttatt gatggcgggg acggacatga tcgagttcac   1920
tacagtagag gagaatatgg cgcattagtt attgatgcta cagccgagac agaaaaaggc   1980
tcatattcag taaaacgcta tgtcggagac agtaaagcat tacatgaaac aattgccacc   2040
caccaaacaa atgttggtaa tcgtgaagaa aaaattgaat atcgtcgtga agatgatcgt   2100
tttcatactg gttatactgt gacggactca ctcaaatcag ttgaagagat cattggttca   2160 caattttaatg atattttcaa aggaagccaa tttgatgatg tgttccatgg tggtaatggt   2220
gtagacacta ttgatggtaa cgatggtgac gatcatttat ttggtggcgc aggcgatgat   2280
gttatcgatg gaggaaacgg taacaatttc cttgttggag aaccggtaa tgatattatc   2340 tcggaggta aagataatga tatttatgtc cataaaacag gcgatggaaa tgattctatt   2400
acagactctg gcggacaaga taaactggca ttttcggatg taaatcttaa agacctcacc   2460
tttaagaaag tagattcttc tctcgaaatc attaatcaaa aaggagaaaa agttcgtatt   2520
gggaattggt tcttagaaga tgatttggct agcacagttg ctaactataa agctacgaat   2580
gaccgaaaaa ttgaggaaat tattggtaaa ggaggagaac gtattacatc agaacaagtt   2640
gataaactga ttaaggaggg taacaatcaa atctctgcag aagcattatc caaagttgtg   2700
```

-continued

```
aatgattaca atacgagtaa agatagacag aacgtatcta atagcttagc aaaattgatt    2760
tcttcagtcg ggagctttac gtcttcctca gactttagga ataatttagg aacatatgtt    2820
ccttcatcaa tagatgtctc gaataatatt caattagcta gagccgctta a             2871
```

<210> SEQ ID NO 3
<211> LENGTH: 26
<212> TYPE: DNA
<213> ORGANISM: Artificial Sequence
<220> FEATURE:
<223> OTHER INFORMATION: Chemically-Synthesized PCR Primer

<400> SEQUENCE: 3

```
gatcgaattc aggatatcac agatct                                           26
```

<210> SEQ ID NO 4
<211> LENGTH: 26
<212> TYPE: DNA
<213> ORGANISM: Artificial Sequence
<220> FEATURE:
<223> OTHER INFORMATION: Chemically-Synthesized PCR Primer

<400> SEQUENCE: 4

```
aattagatct gtgatatcgt gaattc                                           26
```

<210> SEQ ID NO 5
<211> LENGTH: 23
<212> TYPE: DNA
<213> ORGANISM: Artificial Sequence
<220> FEATURE:
<223> OTHER INFORMATION: Chemically-Synthesized PCR Primer

<400> SEQUENCE: 5

```
gaattcaatg cttctggcgt cag                                              23
```

<210> SEQ ID NO 6
<211> LENGTH: 24
<212> TYPE: DNA
<213> ORGANISM: Artificial Sequence
<220> FEATURE:
<223> OTHER INFORMATION: Chemically-Synthesized PCR Primer

<400> SEQUENCE: 6

```
ggtaccggat gagataagat tttc                                             24
```

<210> SEQ ID NO 7
<211> LENGTH: 24
<212> TYPE: DNA
<213> ORGANISM: Artificial Sequence
<220> FEATURE:
<223> OTHER INFORMATION: Chemically-Synthesized PCR Primer

<400> SEQUENCE: 7

```
ggtaccggat gagataagat tttc                                             24
```

<210> SEQ ID NO 8
<211> LENGTH: 24
<212> TYPE: DNA
<213> ORGANISM: Artificial Sequence
<220> FEATURE:
<223> OTHER INFORMATION: Chemically-Synthesized PCR Primer

<400> SEQUENCE: 8

```
gaattcaaga gtttgtagaa acgc                                             24
```

<210> SEQ ID NO 9
<211> LENGTH: 23
<212> TYPE: DNA
<213> ORGANISM: Artificial Sequence
<220> FEATURE:
<223> OTHER INFORMATION: Chemically-Synthesized PCR Primer

<400> SEQUENCE: 9
ggtacctaat ttaccaacac tac                                            23

<210> SEQ ID NO 10
<211> LENGTH: 24
<212> TYPE: DNA
<213> ORGANISM: Artificial Sequence
<220> FEATURE:
<223> OTHER INFORMATION: Chemically-Synthesized PCR Primer

<400> SEQUENCE: 10
ggtaccttat ttgtagagct catc                                           24

<210> SEQ ID NO 11
<211> LENGTH: 31
<212> TYPE: DNA
<213> ORGANISM: Artificial Sequence
<220> FEATURE:
<223> OTHER INFORMATION: Chemically-Synthesized PCR Primer

<400> SEQUENCE: 11
gatatcatgg ctaactctct cagctcgata g                                   31

<210> SEQ ID NO 12
<211> LENGTH: 24
<212> TYPE: DNA
<213> ORGANISM: Artificial Sequence
<220> FEATURE:
<223> OTHER INFORMATION: Chemically-Synthesized PCR Primer

<400> SEQUENCE: 12
ctcgaggcct gccgccacac gttg                                           24

<210> SEQ ID NO 13
<211> LENGTH: 30
<212> TYPE: DNA
<213> ORGANISM: Artificial Sequence
<220> FEATURE:
<223> OTHER INFORMATION: Chemically-Synthesized PCR Primer

<400> SEQUENCE: 13
ctcgagccgc tttcgttctt aaatgttgcg                                     30

<210> SEQ ID NO 14
<211> LENGTH: 29
<212> TYPE: DNA
<213> ORGANISM: Artificial Sequence
<220> FEATURE:
<223> OTHER INFORMATION: Chemically-Synthesized PCR Primer

<400> SEQUENCE: 14
agatcttcac cggctttctg tgcactttg                                      29

<210> SEQ ID NO 15
<211> LENGTH: 30
<212> TYPE: DNA
<213> ORGANISM: Artificial Sequence
<220> FEATURE:
<223> OTHER INFORMATION: Chemically-Synthesized PCR Primer

```
<400> SEQUENCE: 15
gatatcaaat cgtccttaca acaaggattg                                              30

<210> SEQ ID NO 16
<211> LENGTH: 27
<212> TYPE: DNA
<213> ORGANISM: Artificial Sequence
<220> FEATURE:
<223> OTHER INFORMATION: Chemically-Synthesized PCR Primer

<400> SEQUENCE: 16
gaattcacct gaagcgactc gttgggc                                                 27

<210> SEQ ID NO 17
<211> LENGTH: 29
<212> TYPE: DNA
<213> ORGANISM: Artificial
<220> FEATURE:
<223> OTHER INFORMATION: Chemically-Synthesized PCR Primer

<400> SEQUENCE: 17
gaattccctc tttcattctt aaatgtagc                                               29

<210> SEQ ID NO 18
<211> LENGTH: 29
<212> TYPE: DNA
<213> ORGANISM: Artificial Sequence
<220> FEATURE:
<223> OTHER INFORMATION: Chemically-Synthesized PCR Primer

<400> SEQUENCE: 18
agatctgcca tcaataacgg tagtacttg                                               29
```